United States Patent [19]

Long, Jr.

[11] Patent Number: 5,284,645

[45] Date of Patent: * Feb. 8, 1994

[54] FLUOROCARBON EMULSIONS CONTAINING AMINO ACID BASED ANTI-INFLAMATORY AGENTS AND BUFFER SYSTEMS

[75] Inventor: David M. Long, Jr., El Cajon, Calif.

[73] Assignee: Alliance Pharmaceutical Corp., San Diego, Calif.

[ * ] Notice: The portion of the term of this patent subsequent to Jan. 22, 2008 has been disclaimed.

[21] Appl. No.: 417,796

[22] Filed: Oct. 4, 1989

Related U.S. Application Data

[63] Continuation-in-part of Ser. No. 82,846, Aug. 5, 1987, Pat. No. 4,987,154.

[51] Int. Cl.$^5$ .................. A61K 49/04; A61K 31/40; A61K 31/415; A61K 31/435
[52] U.S. Cl. ........................................ 424/5; 424/530; 514/165; 514/264; 514/332; 514/277; 514/396; 514/400; 514/458; 514/420; 514/557; 514/570
[58] Field of Search ............... 514/258, 396, 400, 258, 514/722, 420, 832, 833; 424/5, 530

[56] References Cited

U.S. PATENT DOCUMENTS

| | | | |
|---|---|---|---|
| 4,073,879 | 2/1978 | Long | 424/5 |
| 4,278,654 | 7/1981 | Rakli et al. | 424/5 |
| 4,285,928 | 8/1981 | Wada et al. | 424/5 |
| 4,415,556 | 11/1983 | Bretschneider | 424/153 |
| 4,865,836 | 7/1989 | Long | 424/5 |
| 4,987,154 | 1/1991 | Long | 514/772 |

FOREIGN PATENT DOCUMENTS 517547 8/1981 Australia.
0220153 10/1986 European Pat. Off..

OTHER PUBLICATIONS

Long, David M., Jr., 0307087, 15 Mar. 1989, Bulletin 89/11.
Neiss, Edward S., WO89/00848, 9 Feb. 1989, abstract.
Zipser, R. et al., Circulation Research 47(2): 231-237 (1980).
Saito, H. et al., Nephron 36: 38-45 (1984).
Okegawa, T. et al., J. of Pharmacology and Experimental Therapeutics 225(1): 213-218 (1983).
Schirmer, W. et al., Current Surgery Mar.-Apr.: 102-105 (1987).
Matheson, R. et al., Photochemistry and Photobiology, 21: 165-171 (1975).
Abe, H. et al., Am. J. Physiol. 249: R449-R454 (1985).
Parkhouse, W. S. et al., J. Appl. Physiol. 58(1): 14-17 (1985).

(List continued on next page.)

*Primary Examiner*—Frederick E. Waddell
*Assistant Examiner*—T. J. Criares
*Attorney, Agent, or Firm*—Knobbe, Martens, Olson & Bear

[57] ABSTRACT

Disclosed are fluorocarbon emulsions comprising amino acids and substances related to amino acids, such as substituted amino acids or amphoteric groups of amino acid side chains, for example, the imidazolyl group of histidine. Emulsion formulations comprising imidazole and imidazole based drugs possess anti-inflammatory and antipyretic properties which counteract transient inflammatory responses which occur when these emulsions are administered in vivo. Lipid constituents of histidine-containing emulsions are protected against oxidation caused by free radical formation.

Disclosed also are emulsion formulations buffered with amino acids comprising histidine, imidazole, and related compounds that have a buffering capacity sufficient to maintain the emulsion pH within a specified range under storage conditions and protect these emulsions from the endogenous production of acid. Disclosed also is a method of calculation which assists in the selection of an optimum buffer composition and concentration to preserve physiological compatibility and stability of the emulsions within selected pH limits.

21 Claims, 2 Drawing Sheets

OTHER PUBLICATIONS

Kresh, J. Y. et al., J. of Thoracic and Cardiovascular Surgery, 93(2):309–311 (1987).

Riess, J., Artificial Organs 8(1): 44–56 (1984).

J. Riess et al. Int'l Symposium on Blood Substitutes, Montreal, May (1987).

Ferrari, F. et al., Arch. Int. Pharmacodyn. 277: 303–312 (1985).

Ferrari, F. et al., Psychopharmacology 88: 58–62 (1986).

Maguire, E. and Wallis, R., Thrombosis Research 32: 15–27 (1983).

Kazic, T., European J. of Pharmacology 41: 103–111 (1977).

Ogletree, M. L. et al., J. of Pharmacol. and Exper. Therapeutics 234(2): 435–441 (1985).

Golino, P. et al., Circulation 79: 911–919 (1989).

Cao, Y-Z. et al., Biochem. J. 247: 135–140 (1987).

Aiken, J. et al., Jour. of Pharmacology and Experimental Therapeutics 219(2): 299–308 (1981).

Cadnapaphornchai, P. et al., Amer. J. Physiol. 243: F532–F536 (1982).

Ferrari, F. and G. Baggio, Life Sciences 36: 1397–1405 (1985).

Ferrari, F. et al., Psychopharmacology 93: 19–24 (1987).

Fitgerald, G. A. et al., J. Clin. Invest. 71: 1336–1343 (1983).

Lianos, E. A. et al., J. Clin. Invest. 72: 1439–1448 (1983).

Needleman, P. et al., in Proc. Natl. Acad. Sci. 74(4): 1716–1720 (1977).

Needleman, P. et al., Prostaglandins 14(5): 897–907 (1977).

Needleman, P. et al., J. Clin. Invest. 63: 345–349 (1979).

Nilsson, K. et al., Acta Physiol. Scand. 98: 407–411 (1976).

Patterson, G. A. et al., J. Applied Physiol. 58(3): 892–898 (1985).

Purkerson, M. L. et al., Amer. Proc. Natl. Acad. Sci. USA 82: 193–197 (1985).

Redondo, J. M. et al., Immunology Letters 14: 111–116 (1986/1987).

Tai, H.-H. and B. Yuan, Biochem. Biophys. Res. Commun. 80(1): 236–242 (1978).

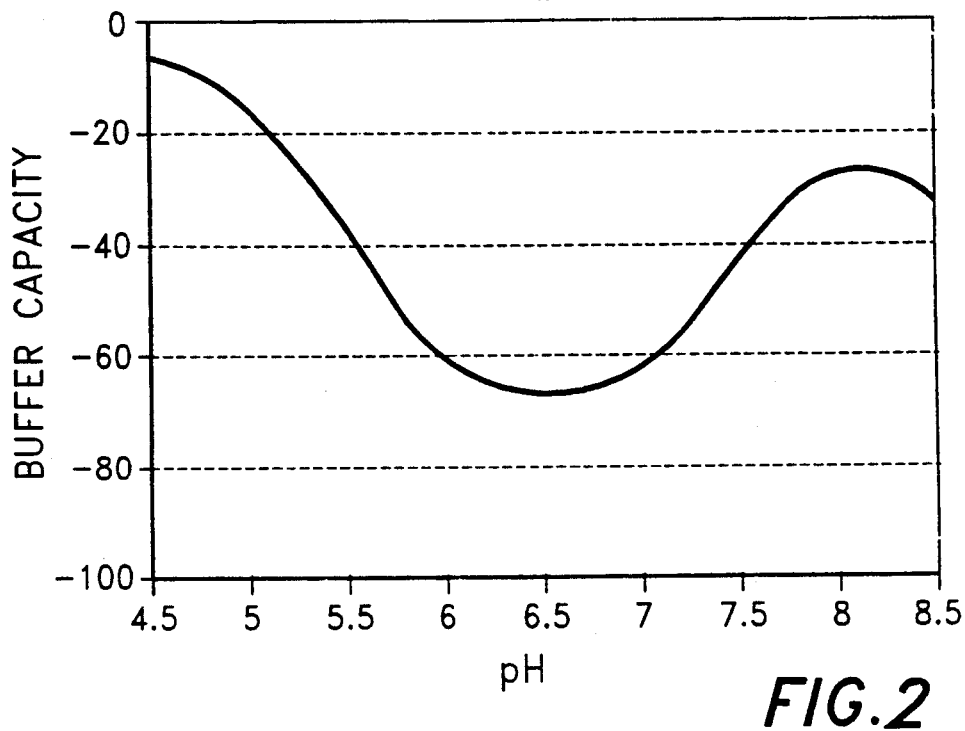
FIG.2
FIG. 3
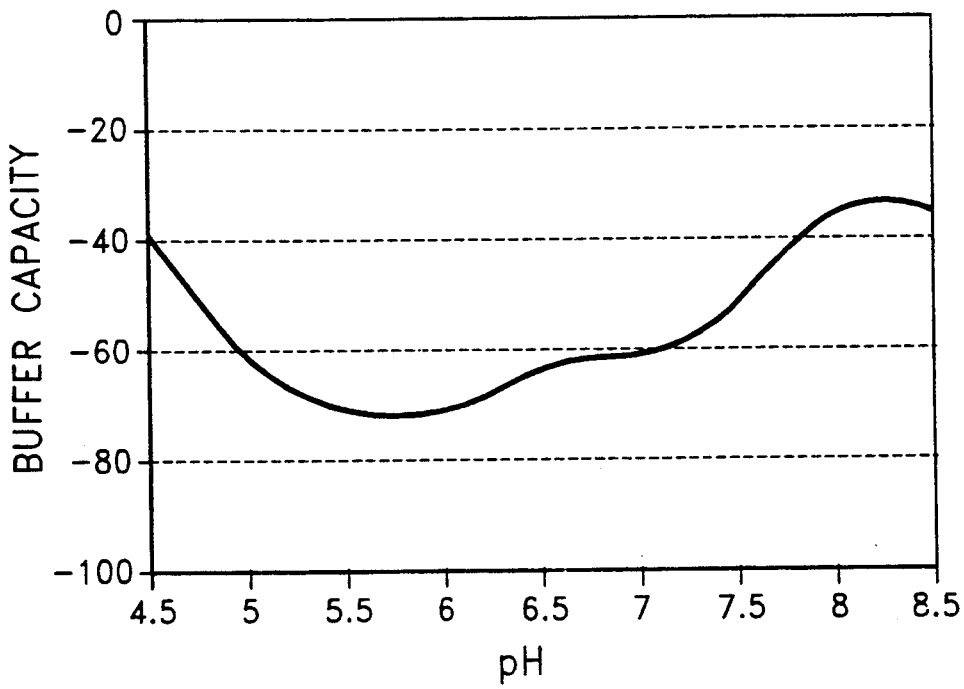

FLUOROCARBON EMULSIONS CONTAINING AMINO ACID BASED ANTI-INFLAMATORY AGENTS AND BUFFER SYSTEMS

This application is a continuation-in-part of application Ser. No. 082,846, filed Aug. 5, 1987 now U.S. Pat. No. 4,987,154.

FIELD OF THE INVENTION

This invention relates to compositions of fluorocarbon emulsions comprising amino acid related agents which enhance the therapeutic effects of the emulsions or promote their stability. It particularly relates to the use of imidazoyl containing compounds as anti-inflammatory agents and to the use of histidine, imidazole and imidazolyl containing compounds, as buffers. This invention also relates to the selection of such buffers, having a defined capacity for neutralizing acid and base within a selected pH range, for use in pharmacological agents, and particularly for use in those agents, such as fluorocarbon emulsions, wherein endogenous processes occurring during storage or delivery generate acids.

BACKGROUND OF THE INVENTION

Imidazole and imidazoyl containing compounds have properties that make them useful in pharmaceutical formulations; for example, imidazole is among the agents which exert a therapeutic effect in alleviating inflammation and tissue injury arising from physiological stress and mediated by prostaglandin end products.

Physiological stress results in an inflammatory response, accompanied by increased prostaglandin synthesis. Phagocytosis of inert particles, bacteria and viruses induces the release of inflammatory hormones and prostaglandins. The stress provoked by reduced oxygen tension, interrupted blood flow, or infections, is often accompanied by increased synthesis of prostaglandins, including the thromboxanes, from arachidonic acid. This synthesis, which occurs primarily in macrophages, begins with the conversion of free arachidonic acid to an alicyclic endoperoxide prostaglandin intermediate, $PGH_2$, by means of a cyclo-oxygenase enzyme. $PGH_2$ is the precursor for several end product prostanoids. Among these are prostacyclin, $PGI_2$, whose formation is catalyzed by prostacyclin synthetase; the active prostaglandins $PGF_{2\alpha}$, $PGE_2$, and $PGD$; and the thromboxane, $TxA_2$, whose formation is catalyzed by thromboxane synthetase. Imidazole inhibits thromboxane synthetase and prevents the synthesis of $TxA_2$; other agents, such as aspirin-like compounds, ibuprofen and indomethacin, inhibit cyclo-oxygenase, thus preventing the synthesis of all the prostanoids.

The prostaglandin end products have several various effects. They can act themselves to alter the pain threshold and, in a manner similar to mediators of the allergic response, to increase capillary permeability. They can also act on cells, primarily macrophages and platelets, to release substances that mediate an inflammatory response, which can involve infiltration of tissues with neutrophils, deposition of immune complexes, edema, and pain.

$PGI_2$ and $TxA_2$ are the most biologically active of the prostanoids, but exert opposite vasoactive and hemodynamic effects. For example, $PGI_2$ is a potent vasodilator and inhibitor of platelet aggregation, whereas $TxA_2$ is a vasoconstrictor and powerful inducer of platelet aggregation. Platelet aggregation results in an inflammatory response, thrombosis, and the unfavorable consequences. In the kidney, for example, thrombosis is followed by glomerulosclerosis, hypertension and cardiac hypertrophy. Imidazole, by selectively inhibiting thromboxane synthetase, shunts the conversion of $PGH_2$ from $TxA_2$ to $PGI_2$, produces physiologically beneficial effects, and reduces tissue damage.

The effect is well demonstrated in the kidney, in which the tissue injury associated with inflammation consists of destruction of the glomerular capsule resulting from vasodilation, followed by deposition of fibrous material. Zipser, R. et al., Circulation Research 47(2): 231-237 (1980), found exaggerated prostaglandin and thromboxane production in the ex vivo perfused kidney, under conditions of renal vein constriction, which could be inhibited by preincubation with imidazole. Saito, H. et al., Nephron 36:38-45 (1984), studied the inhibition of inflammatory damage in the kidney by a specific thromboxane A2 synthetase inhibitor, 1-benzylimidazole (BIm). This agent delayed the progression of glomerulonephritis and in the tissues of treated animals platelet aggregation and fibrin deposits were reduced. Okegawa, T. et al. J. of Pharmacology and Experimental Therapeutics 225(1):213-218 (1983) noted that in endotoxic shock, toxin-stimulated macrophages infiltrate into tissues where they synthesize arachidonate metabolites which modulate an inflammatory response comprising vasodilation, edema and pain. A comparative study of the effectiveness of inflammation suppression by imidazole, indomethacin, and ibuprofen by Schirmer, W et al. Current Surgery March-April, 1987, pp. 102-105) in a model system of acute peritoneal sepsis indicated that imidazole, which inhibits only the formation of thromboxane A2, maintained its activity in preventing endotoxic shock over a longer period of time than the other two agents which act to inhibit the formation of all prostaglandins.

Histidine appears to have a protective effect on fatty acids, which are often present in the emulsifying agents of pharmaceutical preparations. Many medically useful agents are used parenterally in the form of emulsions, comprising a hydrophobic phase dispersed in an aqueous system. The emulsifying agent is commonly a phospholipid, which, because of its amphipathic nature, is able to form a stable association with both phases. Phospholipids are composed of a glycerol group to which fatty acids are attached by ester bonds. Emulsions may, in addition, comprise other types of lipids, some of which also contain fatty acids.

Parenteral emulsions present a particularly difficult buffering problem when they have an emulsifying agent such as phospholipids which comprises fatty acids. Phospholipids and other molecules comprising fatty acids may generate acidic substances after incorporation into emulsions, either while in storage or in use. The acidic substances may be free fatty acids and lysophosphatide species produced either from the hydrolysis of the ester bonds between the glycerol and fatty acid components of phospholipids, or similar free fatty acids resulting from the oxidation of unsaturated fatty acids at the site of their double bonds. Histidine, together with its structurally related amino acid, tryptophan, and sulfur-containing methionine, appears to be responsible for the ability of some proteins to quench singlet oxygen produced by photosynthetic processes and by this means to prevent their own oxidative decomposition. The rate of physical quenching is the same for both free amino acids and those incorporated into a protein structure. (Matheson, R. et al., *Photochemistry and Photobiology*, 21:165-171 (1975)). It is quite probable that histidine would be similarly effective in preventing the oxidative degradation of phospholipid fatty acids (or free fatty acids) which leads to acid generation and a decrease in pH in fluorocarbon emulsions.

With the exception of the stomach, the pH range in the body is maintained, through chemical exchanges occurring principally in the renal and respiratory systems, at about 6.4 to 7.5 for the tissues and between 7.35 and 7.45 for the extracellular fluids. Most physiological processes and biochemical reactions occur then within relatively narrow pH limits. Little is known about the rates of enzyme reactions at physiological pH. The physiological pH restriction may provide an optimum pH range for the rates of certain enzyme reactions, and may act as a control mechanism for those for which that pH is not optimum.

It is clear, however, that processes in some tissues and organs are sensitive to small changes in pH. The effect of an acid environment on the heart is an example. As the pH of arterial blood falls, the coronary vessels dilate to increase blood flow and a supply of oxygen to the cardiac muscle; at a critically low pH, there is a sudden, sharp decrease in myocardial contractility. In dogs, the lethal pH is 6.0, at which point there is cardiac arrest in extreme diastole. The effect is independent of the nature of the anion species of the acid. Another example is an effect such as occurs in metabolic alkalosis, wherein an increase in the pH of the blood moves extracellular fluid into the cells, resulting in tissue edema.

It is important then that substances introduced parenterally into the body, and particularly those placed in the circulation, most critically the cardiac circulation, are buffered to a physiological pH, so as not to disturb the biochemical balance. It is further important that the agents used to buffer these substances are physiologically innocuous.

The natural physiological buffering agents are principally carbonate and phosphate ions and the amino acids. In the blood the buffers $NaHCO_3/H_2CO_3$ along with constituent blood proteins hemoglobin, oxyhemoglobin, albumin and globulin and $Na_2HPO_4/NaH_2PO_4$ resist changes in pH. Proteins may contain groups which act as buffers, depending on the pH; these are commonly the carboxyl groups of glutamic and aspartic acids and the amino groups of lysine, the guanido group of arginine and the imidazolyl group of histidine.

Because of their natural buffering capacity, carbonates and phosphate salts are commonly used as buffers in intravenous solutions. A difficulty with these buffers that becomes more significant in highly buffered solutions, is that both carbonate and phosphate ions form insoluble precipitates with divalent cations such as magnesium and calcium. This has two undesirable effects. First, it reduces cation concentrations and inhibits critical metabolic processes, such as $Mg^{++}$ dependent enzyme reactions, and $Ca^{++}$ dependent muscular contractions. Secondly, the insoluble precipitates formed can block the blood flow through small vessels, and those formed when solutions are introduced into cavities such as the brain ventricles can deposit a film on internal membrane surfaces which will then interfere with membrane transport.

Amino acids may be advantageously used as buffers in pharmaceutical applications because they have neither of these undesirable actions, and they are, in addition, metabolizable, nutritive substances.

Histidine appears to act as a natural buffer in tissue such as muscle where high metabolic activity occurs. The process of anaerobic glycolysis necessary for rapid ATP production in exerted muscle is associated with elevated lactate, proton accumulation and a fall in pH. Abe, H. et al., *Am. J. Physiol.* 249:R449-R454 (1985), found that histidine and histidine-containing dipeptides are the principal buffers in the skeletal muscle of fish such as marlin that has a high activity pattern, and that the histidine buffered tissue had a higher buffering capacity than corresponding tissue from less active fish. In a parallel study on humans, Parkhouse, W. S. et al., *J. Appl. Physiol.* 58(1):14-17 (1985). found higher buffering capacity and higher levels of histidine related peptides in needle biopsies of muscle tissue from athletes capable of superior high-intensity running performance.

Histidine has been used as a buffer for cardioplegic solutions which are used to preserve organs such as hearts and kidneys during surgical procedures in which ischemic intervals occur and during transplant procedures. Bretschneider U.S. Pat. No. 4,415,556. The composition of these solutions has been determined empirically to comprise substances normally found in blood and electrolytes favorable to preserving the contractility of cardiac muscle and preventing edema. Histidine content is adjusted so that the solutions provide the pH and pH buffering capacity of cardiac tissue as determined by comparative manual titrations. (Kresh, J. Y. et al., *J. of Thoracic and Cardiovascular Surgery*, 93(2):309-311 (1987)).

One problem in buffering lipid containing emulsions is that acid generating oxidative processes, which occur to an unpredictable extent, may exceed the buffering capacity of the solution, and bring the pH down to unacceptably low levels.

One approach to this problem has been to prepare an emulsion and add sufficient sodium hydroxide or other inorganic base to the preparation to achieve an initial pH high enough to anticipate a degree of acid generation. However, this method of protection, high formulation pH, can actually accelerate the degradation of the lipids and aggravate the problem it is intended to correct.

Presuming one could predict the amount of expected proton generation in a lipid-containing emulsion, it would still not be possible to provide the necessary buffering capacity to the emulsion accurately enough so as to assure its pH stability within an acceptable range using present methods.

The major difficulty is that there is no theoretical mathematical expression for the titration curve of a polyprotic acid or base, and hence no way to calculate the buffer capacity of these substances exactly. The present method of calculating buffer capacity depends on the use of the Henderson-Hasselbach equation. This expression, $$pH = pK_a + \log \frac{[Ac^-]}{[HAc]},$$

relates the pH to the ionization constant for a single ionizable group of a weak acid or base. Buffer capacity can be determined for that ionizable group by calculating the change in the log $Ac^-/HAc$ term corresponding to a change in the pH. One of the shortcomings of this method is that it can only provide an approximation of the buffering capacity of a polyprotic buffer or a mixture of buffers having different p$K_a$'s, because the buffering capacity of each ionizable group must be calculated independently, and the interaction between these groups ignored. When the p$K_a$'s are quite different, the error is negligible (but not zero); but when they are close in value, the mis-estimation is serious.

The pK is that pH at which a weak acid or base is 50% converted to its salt, and it is at this point that its buffering capacity, the amount of $H^+$ or $OH^-$ ions it can neutralize per unit change in pH, is highest. Histidine is one of the most effective amino acid buffers for parenteral use because it contains an imidazole ring having a nitrogen site with a pK of about 6.83, near the center of the physiological pH range. Imidazole itself, in which the pK at the nitrogen site is about 6.99, also acts as a buffer.

A determination of the optimal agent for providing the required buffer capacity by the trial and error process of manual titration would be tedious and expensive and particularly difficult if a combination of amino acids were used.

Further, an exact determination of the necessary buffering capacity in the emulsion must take into consideration the influence of the ionizable groups of the phospholipid species present. Although the effect of these groups is negligible at neutrality, having p$K_a$'s of 1-2 and 10-13 for most species, the effect is also not zero. These effects cannot be determined manually, because the titration of the buffer with acid or base would hydrolyze the lipid components, generating interfering acid or base.

The emulsions cannot be adequately buffered simply by adding an excess of an amino acid buffer, because the constraint that all administered parenteral agents must be isotonic limits the amount of amino acid that can be added to the emulsion. For that reason it is important to determine precisely the effective amount of these agents in the emulsions.

Amino acids such as histidine and other structures containing an imidazolyl group appear to be particularly appropriate buffering agents for fluorocarbon emulsions. Moreover, the anti-inflammatory properties of imidazole and the anti-oxidative properties of histidine can provide further advantages when incorporated in fluorocarbon formulations.

Fluorocarbon emulsions can be widely used intravascularly and extravascularly as contrast agents. Further, fluorocarbons have the capacity to dissolve high concentrations of oxygen, making them suitable as artificial blood and as oxygen transport agents in the treatment of local ischemias. However, the intravascular administration of fluorocarbon emulsions is frequently accompanied by a transient fever and inflammatory response. I have found that agents such as imidazole, ibuprofen and indomethacin have an anti-pyretic effect which mitigates the inflammatory response when they are present in these emulsions.

For all the foregoing reasons, amino acids such as histidine and its constituent imidazolyl group are believed to be particularly effective pharmacological components as well as appropriate buffering agents for fluorocarbon emulsions.

It is therefore an object of the invention to provide formulations for fluorocarbon emulsions comprising an effective therapeutic concentration of imidazole or related pharmacologically active agents.

It is desirable to provide formulations for fluorocarbon emulsions which are protected against decomposition by the use of effective buffers and antioxidants. It is therefore further an object of the invention to provide formulations for fluorocarbon emulsions comprising effective buffering concentration of amino acids, and particularly histidine and related compounds comprising an imidazolyl group.

It is further an object of the invention to provide a method for selecting buffers for formulations of fluorocarbon emulsions, comprising amino acids which provide a known buffering capacity for those emulsions within a given pH range.

It is further an object of the invention to provide formulations of amino acid buffered fluorocarbon emulsions which are stable within a physiological pH range during a sterilization process and for an estimated period of storage.

DESCRIPTION OF THE DRAWINGS

FIG. 2 is a graph of the titration of histidine and imidazole.

FIG. 3 is a graph of the titration of histidine and methyl histidine.

SUMMARY OF THE INVENTION

Figure 1A:
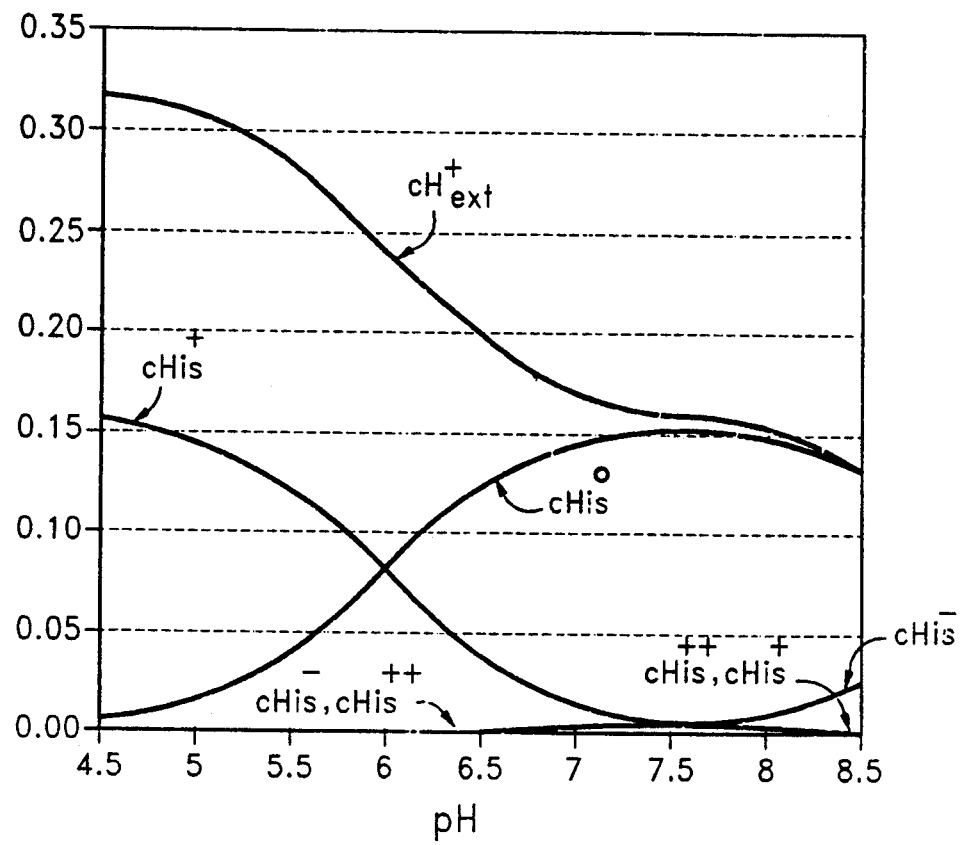
FIG. 1a is a graph of the titration of histidine.

The present invention provides fluorocarbon emulsions comprising an effective amount of a therapeutic agent which is imidazole, an imidazole based drug, or combinations thereof. The present invention also provides formulations of fluorocarbon emulsions comprising amino acid buffers which are selected to retain the emulsions within a physiological pH range during storage despite the endogenous generation of acidic (or basic) substances.

There is also provided a method for selecting an optimal amino acid related compound or a combination of these for use as a buffer in a formulation comprising a fluorocarbon emulsion. The method for optimization comprises matching the buffering capacity of the buffer with respect to both its ionization constants and concentration to a defined physiological pH range and the potential proton generating (or proton absorbing) ability of the formulation.

Thus, in accordance with one object of the invention, there is provided a fluorocarbon emulsion for use in the tissues, organs and cavities of the body, comprising an aqueous phase, an effective amount of at least one anti-inflammatory agent which is imidazole, a drug having a chemical structure which includes an imidazolyl group, or combinations thereof; an effective amount of a fluorocarbon; and an emulsifying agent. In a preferred embodiment, the emulsion also comprises an oligopeptide, an amino acid, a substituted amino acid or combinations thereof. In other preferred embodiments, the anti-inflammatory agent is an inhibitor of thromboxane synthetase, cyclooxygenase, or an inhibitor of both enzymes. In a particularly preferred embodiment, the therapeutic agent is N(7-carboxyheptyl)imidazole, 4-(2-(1-H-imidazol-1-yl)ethoxy)benzoic acid (dazoxiben) or imidazo(1,5-α)pyridine-5-hexanoic acid (CGS 13080). The fluorocarbon emulsion may further comprise an anti-inflammatory agent which is aspirin, indomethacin, or ibuprofen. The emulsion can be one which is capable of carrying oxygen to the tissues.

According to another aspect of the invention, there is provided a method of treatment of the medical conditions of sepsis, endotoxin shock, hemorrhagic shock or blood loss, pulmonary hypertension or other complications of sepsis, or thrombosis, for example, following thrombolysis for acute myocardial infarction, comprising the introduction of such emulsions into the bloodstream of an animal. In other preferred embodiments, the emulsions of the present invention are used in a method for reducing fever, anorexia, and malaise during administration of fluorocarbon emulsions into an animal, comprising the step of including in the emulsion imidazole or an imidazole-based thromboxane synthetase inhibitor, cyclooxygenase inhibitor or phosphodiesterase activator.

According to another aspect of the invention, there is provided a fluorocarbon emulsion for use in the tissues, organs and cavities of the body, comprising a continuous aqueous phase; an effective amount of a fluorocarbon compound; an effective amount of an emulsifying agent; and a buffer, selected from the group consisting of amino acids, oligopeptides, substituted amino acids, the amphoteric groups of amino acid side chains, and mixtures thereof. In a preferred embodiment, the buffer is selected from the group consisting of histidine, imidazole, substituted histidine and imidazole compounds retaining the amphoteric site of the imidazole ring, oligopeptides containing histidine, and mixtures thereof. In a particularly preferred embodiment, the buffer comprises a mixture of histidine and imidazole. The concentration of imidazole in the emulsion is preferably between about 0.01 molar and 0.2 molar and the concentration of histidine is between about 0.01 molar and 0.2 molar. In preferred embodiments of the invention, the pH of the fluorocarbon emulsion is maintained by the buffer between about 5.3 and 8.9. In a preferred embodiment, the pH is maintained between about 7.3 and 7.9. The pH may be measured at a physiological temperature of about 37° C., or at a room temperature below about 30° C. In a particularly preferred embodiment, the concentration of the buffer is sufficient to provide a buffering capacity of at least 20 mmol/L for each pH unit between pH values of 5.3 to 8.9. In one embodiment of the invention, the fluorocarbon emulsion comprises a brominated perfluorocarbon; in another the fluorocarbon emulsion comprises a perfluorocarbon hydride. In a preferred embodiment, the fluorocarbon compound is present at from about 40% to 125% weight/volume (w/v) in grams percent. In a particularly preferred embodiment, the fluorocarbon compound is present at from about 75% w/v.

In another preferred embodiment, the fluorocarbon is emulsified by means of an effective amount of a phospholipid. Alternatively, the emulsifying agent of the fluorocarbon formulation may be a nonionic surfactant or a fluorinated surfactant. In preferred embodiments, the fluorocarbon emulsion may further comprise an antioxidant, a steroid compound, and an osmotic agent. In particularly preferred embodiments, the antioxidant is a tocopherol, the steroid is cholesterol, and the osmotic agent is a polyhydroxyl compound.

The present invention also includes a method for selecting an effective buffer for a fluorocarbon emulsion from the group consisting of amino acids, oligopeptides, substituted amino acids, the amphoteric groups of amino acid side chains, or mixtures thereof, comprising estimating the amount of acid or base which can be produced from components of the emulsion by endogenous chemical processes; selecting an acceptable pH range in which the emulsion is to be maintained; selecting a maximum acceptable concentration for the buffer, and selecting from the group a buffer having the capacity to maintain said emulsion within said range in the event of said endogenous chemical processes, while the concentration of the buffer is below the defined maximum acceptable concentration. In a preferred embodiment, the buffer comprises at least one amino acid having three amphoteric groups. In particularly preferred embodiments, the buffer is selected from a group consisting of histidine, imidazole, substituted histidine and imidazole compounds retaining the amphoteric site of the imidazole ring, oligopeptides containing histidine and mixtures thereof. In preferred embodiments, at least one buffering agent is 1-methyl-histidine, 1-methyl-imidazole, anserine or carnosine. In other preferred embodiments, the buffer is a mixture of histidine and imidazole. In a most preferred embodiment, the concentration of imidazole is between about 0.01 molar and 0.2 molar and the concentration of histidine is also between about 0.01 molar and 0.2 molar. In a preferred embodiment, the method selects a buffer which can maintain the pH of the fluorocarbon emulsion between about 5.3 and 8.9. In another embodiment, the method selects a buffer which can maintain the pH within a physiologically acceptable range. In a preferred embodiment, the physiological range lies between pH values of 7.3 and 7.9. The method can select buffers which can maintain the pH of the fluorocarbon emulsion at a physiological temperature of, for example, 37° C., or at a storage temperature below about 30° C. In a particularly preferred embodiment, the method selects a buffer of a composition and concentration below an acceptable maximum sufficient to maintain the fluorocarbon within the pH range when at least 10% of the total potential endogenous acid (or base) is generated. In a most preferred embodiment, the buffer has a buffering capacity of at least 20 mmol/L for each pH unit throughout the selected pH range.

DETAILED DESCRIPTION OF THE PREFERRED EMBODIMENT

The formulations of the present invention comprise fluorocarbon emulsions made up of a fluorocarbon having from about 6 to 18 carbon atoms, an aqueous phase, and an emulsifying agent, the emulsion being maintained within a defined pH range by an amino acid buffer. Fluorocarbons have the capacity to dissolve oxygen and are therefore useful as transport agents to supply oxygen to ischemic tissues in the body. Other physical properties of fluorocarbons also make them useful as contrast agents for radiography, computer assisted tomography (CAT scan), ultrasonography, and magnetic resonance imaging (MRI). Fluorocarbon compounds are oils and are therefore immiscible with body fluids. Emulsification makes it possible to introduce these substances into the circulatory system of the body in a readily dispersible form in which the fluorocarbon droplets are coated with an amphipathic substance.

Fluorocarbon molecules used in these emulsions may have various structures, either straight or branched chain or cyclic, as described in Riess, J., Artificial Organs 8(1):44–56 (1984). These molecules may also have some degree of unsaturation, and may also contain bromine or hydrogen atoms, or they may be amine derivatives. The fluorocarbons may be present in the emulsion in useful concentration ranging from about 25% to 125% weight per volume (w/v). As used throughout, concentrations defined as weight/volume are understood to represent grams/ml and % weight per volume to represent grams/100 ml.

Emulsions having various concentrations of fluorocarbon are useful in different applications, for example, when used as contrast media, for treating ischemia, or when applied intravascularly or within cavities of the body. Accordingly, useful formulations of the present invention will include those having fluorocarbon concentration in ranges greater than 40%, 50%, 55%, 60%, 75% or 80% w/v. Preferred fluorocarbon emulsion formulations are those disclosed in U.S. patent application Ser. Nos. 818,690; 82,846; 114,075; 140,543; and 234,193 (D. M. Long, Jr.), which are hereby incorporated by reference. The higher concentration emulsions are desirable for their efficiency in transporting oxygen or when used intravascularly to provide contrast for radiographic studies. Low concentration emulsions may be useful in imaging large body volumes. Emulsion fluorocarbon concentrations are limited by the capacity of the emulsifying agent used, the efficiency of the emulsification process, and by a limiting viscosity.

Emulsifying agents may be anionic, cationic or nonionic surfactants or combinations thereof as are well known to those in the chemical arts or they may be mixtures of synthetic compounds such as Pluronic F-68 TM, a condensate of ethylene oxide with propylene glycol, as used in Long U.S. Pat. No. 4,073,879. Fluorosurfactants, such as those described by J. Riess et al. Int'l Symposium on Blood Substitutes, Montreal, May, 1987, are particularly suitable can also be used. Emulsifying agents may also be mixtures of the above agents. Alternatively, emulsifiers may be natural amphipathic compounds such as phospholipids, particularly phosphatidylcholine, wherein combined hydrophilic and hydrophobic properties enable the molecule to interface with both aqueous and fluorocarbon systems, thereby forming the emulsion droplets. There are various species of each class of phospholipids, such as the phospholipid cholines, comprising various pairings of saturated and unsaturated fatty acids in the glycerol structures. Phosphatidylcholine is an abundant natural material (lecithin) which may be purified from egg yolk, or may be produced synthetically (Avanti Polar Lipids, Pelham, Ala.).

The phospholipid emulsifying agent should be included in the range of from 2 to 14% w/v, increasing the phospholipid concentration with increasing fluorocarbon concentration. The preferred amount for an emulsion comprising 75% w/v bromofluorocarbon is 2.5 to 5% w/v and 3.5 to 10% w/v of phospholipid for an emulsion with 100% w/v bromofluorocarbon. In a preferred embodiment, the phospholipid comprises at least 2% w/v of the emulsion.

Emulsification requires large amounts of energy to convert a two-phase immiscible system into a suspension of discontinuous small droplets of hydrophobic fluid in an aqueous continuous phase. Fluorocarbon emulsification may be carried out generally by either of two general processes which provide energy to the system to break up the fluorocarbon volume into small droplets. In sonication emulsification, a probe is inserted into the mixture of fluorocarbon, emulsifier, and aqueous phase, and bursts of energy are released from the tip of the probe. In a mechanical emulsification process, such as performed by a Microfluidizer ® apparatus (Microfluidics, Newton, Mass. 02164), streams of the mixed emulsion components are directed through the apparatus at high velocity and under high pressure (e.g. 15,000 psi), and the high shear forces or cavitation resulting from the mechanical stress applied to the fluid produce the emulsion.

The aqueous phase of the emulsion may have components dissolved therein which give the emulsions desirable properties. For example, it may comprise an osmotic agent to bring the emulsion to physiological isotonicity. The osmotic agent may be sodium chloride, or it may be a polyhydroxyl compound, such as a sugar or mannitol. The aqueous phase will also contain soluble buffering agents.

The lipid phase of the emulsion may also have components dissolved therein. For example, a phosphatidyl choline emulsifier may have glycerol, phosphatidyl glycerol, other phospholipids or cholesterol admixed, and further contain an antioxidant substance, such as a tocopherol, to protect against lipid oxidation.

Either the aqueous or the non-aqueous phase of the emulsion may also comprise a drug or a diagnostic agent.

Amino acids are valuable as additives to fluorocarbon emulsions. Since they are natural constituents of proteins, they are physiologically innocuous, and further, provide nutritive value. One amino acid derivative, imidazole, can also serve as a pharmacologically effective agent which ameliorates the pyretic and inflammatory responses of subjects as described above. It is particularly advantageous for use in emulsions administered to those subjects in whom the macrophages are primed to produce inflammatory responses such as subjects bearing malignant tumors, or victims of septic or hemorrhagic shock. The amino acid, histidine, appears to exert a protective effect on the lipid constituents of the lipid emulsifiers. Finally, amino acids are useful buffers for fluorocarbon emulsions.

Imidazole, a nitrogen containing cyclic radical, present in the side chain of the amino acid histidine, has therapeutic properties, including anti-inflammatory effects as indicated above, and we have found that as such, it may be usefully incorporated into fluorocarbon emulsions.

The therapeutic effects of imidazole appear to flow from a number of physiological mechanisms. One mechanism, underlying its anti-inflammatory effect, is related to its ability to inhibit the production of prostaglandins.

Macrophages from tumor-bearing rats are known to produce larger quantities of prostaglandins in the resting state and to respond to stimulation with a severalfold greater increase in prostaglandins than do macrophages from normal rats. These prostaglandins are endogenous pyrogens, and are implicated in symptoms experienced by subjects, particularly those with malignant tumors, during the administration of fluorocarbon emulsions. Fluorocarbon emulsions probably serve as stimulants for the release of macrophage hormones, particularly in tumor-bearing subjects. Their administration to rabbits and humans with malignant tumors results in a flu-like syndrome of fever, anorexia, malaise and myalgia, not observed in similarly treated normal rabbits. It has been found that the symptoms can be alleviated by cyclo-oxygenase inhibitors such as ibuprofen. The data of Examples 1, 2 and 3 indicate that the thromboxane synthetase-inhibiting action of imidazole incorporated into 100% (w/v) perfluorooctyl bromide emulsions administered to tumor-bearing rabbits acts to prevent the pyrogenic response in a manner similar to its protective action seen in endotoxic shock and ischemia. This action of imidazole probably prevents the stimulation of macrophages and the consequent release of prostaglandins and thromboxane. The data of Example 4 indicates further that blood chemistries are less affected by therapies involving the use of fluorocarbon emulsions buffered with histidine and imidazole as compared to Tham.

Imidazole has also been shown to have an antidepressant effect (Ferrari et al. *Arch. Int. Pharmacodyn.* 277:303-312 (1985); *Psychopharmacology* 88:58-62 (1986)), which could make it an advantageous adjunct to therapy in many of the patients to whom fluorocarbon emulsions are administered. Accordingly, a preferred embodiment of the invention comprises a fluorocarbon emulsion having at least 0.01% (w/v) imidazole. Effective imidazole concentrations in fluorocarbon emulsions vary according to the application, but are conveniently from about 0.01 to 3.0% (w/v) or grams percent. In a preferred embodiment, the imidazole concentration is about 1.5% (w/v).

Experimental work indicates that drugs which are imidazole derivatives, such as N(7-carboxyheptyl)imidazole, 4-(2-(1H-imidazol-1-yl)ethoxy)benzoic acid (dazoxiben), and imidazo(1,5- pyridine-5-hexanoic acid (CGS 13080), (Ciba-Geigy, West Sussex, United Kingdom) act effectively to inhibit thromboxane synthetase in the rat (Maguire, E. and Wallis, R., *Thrombosis Research* 32:15-27 (1983), and these drugs may be similarly incorporated into fluorocarbon emulsions in comparable concentrations.

Imidazole and imidazolyl containing compounds also exert a beneficial anti-inflammatory effect by activating phosphodiesterase which in turn affects the level of cyclic adenosine 3',5'-monophosphate (cAMP). The physiological effect of such activation is the contraction of smooth muscle, opposing the vasodilation of inflammation. The imidazole phosphodiesterase-activating effect also enhances the contractility of smooth muscle in response to histidine (Kazic, T. *Amer. J. of Pharmacology* 41:103-111 (1977). Accordingly, imidazole and histidine present in fluorocarbon emulsion can act synergistically to reduce the observed transient febrile response. Since histidine appears to have the ability to prevent the oxidation of unsaturated fatty acids present in the emulsifier, its presence in the fluorocarbon emulsion will retard the acidification of the emulsifier and the production of toxic lysolecithins, thus independently opposing an inflammatory response. In the use of both imidazole and histidine, the useful concentration is limited only by osmotic and solubility effects, because these substances are physiologically well tolerated. However, in a preferred embodiment, fluorocarbon emulsions comprise at least 0.01% (w/v) and up to about 3.0% (w/v) histidine in addition to at least 0.01% (w/v) of imidazole. In a more preferred embodiment, the concentration of histidine in the emulsion is about 0.3% (w/v).

Other anti-inflammatory agents, comprising aspirin (acetylsalicylic acid) or other salicylates, indomethacin (1-(p-chlorobenzoyl)-5-methoxy-2-methylindole-3-acetic acid) and ibuprofen (($\pm$)-2-(p-isobutylphenyl)-propionic acid) may usefully be added to imidazole or histidine-containing fluorocarbon emulsions in established therapeutic concentrations to enhance the anti-inflammatory effects thereof. Accordingly, these drugs may be added to fluorocarbon emulsions of the invention in amounts sufficient to establish a total dose of 300 to 1000 mg of aspirin; 200 to 1200 mg of ibuprofen; and 10 to 100 mg of indomethacin.

Other agents are available which inhibit an inflammatory response by potent and selective biological actions. One of these is SQ 29,548, [1S-[1$\alpha$, 2 $\beta$(5 Z), 3 $\beta$, 4 $\alpha$]]-7-[3-[[2-[phenylamino)carbonyl]hydrazino]methyl]-7-oxabicyclo[2.2.1]hept-2-yl]-5-heptenoic acid (Squibb Institute for Medical Research, Princeton, N.J.) which acts to inhibit vasoconstriction and platelet aggregation by blockade or antagonism of thromboxane $A_2$ receptors. The pharmacology of SQ 29,548 is described by Ogletree, M. L. et al. *Jour. of Pharmacol. and Exper. Therapeutics* 234(2):435-441 (1985). Another is LY53857 (Eli Lilly, Indianapolis, Ind.) which acts by blockade or antagonism of serotonin receptors. The action of LY53857 is described in Golino, P. et al. *Circulation* 79 911-919 (1989). These drugs may be usefully incorporated into the fluorocarbon emulsions of the invention separately or together in doses of about 0.2 mg/kg body weight for each drug.

In a most preferred embodiment, the emulsion further comprises a minor amount of a tocopherol, preferably from alpha-D-tocopherol. Tocopherols are known to inhibit lipid oxidation and in the context of in vivo activity, has the dual effect of protecting the integrity of lipids, particularly those of cell membranes, as well as protecting the organism against the toxic and cytolytic effects of deacylated phospholipids, the lysophosphatides, most commonly lysolecithin, which can accumulate in tissue following oxidative events (Cao, Y-Z. et al., *Biochem. J.* 247:1325-140 (1987). Effective, oxidation-preventing amounts of tocopherols in the fluorocarbon emulsions are from 0.01% to 0.5% (w/v) of a tocopherol or an equivalent amount of a tocopherol ester. We have found that alpha-D-tocopherol, dietary vitamin E, synergistically promotes the anti-pyretic effect of imidazole-containing fluorocarbon emulsions as indicated in Example 1.

Histidine alone, in concentrations of from 0.01% to 3.0% (w/v) in fluorocarbon emulsions can be used to stabilize fluorocarbon emulsions comprising lipid emulsifiers by virtue of its ability to absorb free radicals and retard oxidative processes.

AMINO ACID BASED BUFFER SYSTEMS

The requirement in many cases for a fluorocarbon emulsion buffer is that it be capable of maintaining a physiological pH from the time the emulsion is manufactured until it is administered. If an emulsion is manufactured for in vivo use, it is sterilized after formulation and emulsification, and as with most injectables, stored sealed until use. The sealed emulsions may be refrigerated at temperatures above freezing, or stored at room temperatures. During this period chemical processes occurring in the emulsion can generate acid, tending to lower the pH. A particular problem occurs in the case of phospholipid emulsifiers, which are subject to acid-generating fatty acid decomposition. The pH of emulsions thus prepared can fall when ester groups linking the fatty acid components to the glycerol of the phospholipid become hydrolyzed, or when regions of unsaturation in these fatty acids undergo oxidation, whether the fatty acid has been hydrolyzed or not. The buffer capacity of an effective emulsion buffer, that is, its ability to resist pH change in the event of added acid or base, must be high enough to anticipate and neutralize these hydrolytic and oxidative events.

In order to add sufficient buffer to the emulsion, the maximum amount of acid or base which can be generated during a storage interval must be predicted either by calculation or by empirical determination. One can, for example, knowing the $pK_a$ value of constituent fatty acids or their oxidation products, and their concentration in the emulsion, predict the total $H^+$ generating capacity. Alternatively, the total $H^+$ can be determined for a representative sample of the emulsion by exhaustive hydrolysis and oxidation through accelerated ageing procedures known to those in the art, such as, for example, exposure to elevated temperature, pressure and oxygen tensions, following by quantitative neutralization.

The amount of acid (or base) that must potentially be neutralized, together with the pH limits for the formulation are the determining factors in the selection of a suitable buffer. Another requirement is that the concentration of the buffering agent and hence its contribution to the osmolarity of the final emulsion should be limited so that the emulsion does not exceed physiologically acceptable values of approximately 300 to 350 mOsm (milliosmols). This requirement may often impose stringent concentration limitations. For this reason the agent used as a buffer should be efficient with respect to its specific buffering capacity within the pH range to be buffered, that is, the mmoles of acid/pH/mg of buffer.

All amino acids are capable of acting as buffers because their constituent terminal amino and carboxyl groups are amphoteric, acting as weakly ionizable acids and bases capable of releasing or absorbing protons. However, the ionization constants ($pK_a$'s) for these terminal groups are such that they exert a buffering action most effectively at pH extremes below 2 and above 9. Amino acids that have a third amphoteric group, such as, for example, the carboxyl groups of glutamic and aspartic acids and the amino groups of lysine, the guanido group of arginine and the imidazolyl group of histidine, are more preferred for physiological buffering (pH range of from 6.4 to 7.5), since the $pK_a$'s for these groups are closer to neutrality. Unfortunately, none of the amphoteric groups of amino acids has a $pK_a$ squarely within this range. The most suitable and most preferred amino acid for physiological buffering purposes is histidine, which contains an imidazolyl ring whose imide group has a $pK_a$ of 6.00. Imidazole itself, in which the $pK_a$ of the imide nitrogen is shifted to 6.99, is equally preferred.

A buffer acts most efficiently when the pH of the solution corresponds closely to the $pK_a$ of one of its ionizable groups. For example, the imidazolyl group of histidine, with a $pK_a$ of 6.00, buffers more effectively at pH 6 than it does at pH 7. As the pH of the solution moves away from the $pK_a$, buffering capacity may decrease markedly.

It is often difficult to get maximum buffering capacity directly by matching the $pK_a$ of a buffer to a pH requirement. However, buffering capacity at one pH region may be increased by combining two buffering agents with $pK_a$'s which closely bracket the required pH; for example, a mixture of histidine with a $pK_a$ of 6.00 and cystine with a $pK_a$ of 7.85 will buffer at pH 7.00 more effectively than either agent alone. Another approach is to use derivatives of amino acids in which the $pK_a$ is slightly shifted. For example, a $pK_a$ of the imide group of imidazole, (imidazole lacks the glycine group of histidine), is at a $pK_a$ of 6.99, almost one unit closer to neutrality than the corresponding imide group of histidine. Derivatives of amino acids which shift corresponding $pK_a$'s comprise products of methylation or acetylation, or other common synthetic processes. Useful derivatives of amino groups are also the characteristic radical groups of specific amino acids having an amphoteric site, for example, the imidazole group of histidine, or the guanido group of arginine. The amphoteric site of these isolated radicals has a pH which is shifted slightly from that of the same radical incorporated into the amino acid. Corresponding $pK_a$'s are also shifted when amino acids are condensed into peptides, and for this reason, dipeptide or other small peptides comprising desirable amino acid buffers, such as histidine, may be more effective in some pH ranges than the parent species. By using amino acids and their derivatives in these ways, adjusting $pK_a$'s and combining buffers effectively, it is possible to provide more buffering capacity within a pH interval without increasing the total buffer concentration.

For some purposes, it may not be necessary to maintain the pH of the emulsion within a physiological range, but only within a range that will insure the chemical integrity of the components, for example, a pH of 5.3 to 8.9. A buffer concentration may also be reduced to maintain a defined pH to the extent of partial endogenous acid production, for example, a maximum of 10%. On the other hand, some applications, for example, when a fluorocarbon emulsion is used to perfuse the cardiac tissues, may have more stringent buffering requirements, wherein the pH may have to be maintained between 7.3 and 7.9.

The method of calculation and computer program below provide a method which makes it easier to select the most efficient amino acid buffering system to provide a defined buffering capacity within a defined pH range. The program, based on the calculations, computes the buffering capacity, at regular pH intervals, for any buffer or mixture of buffers for which the $pK_a$ and concentration are input. Using this information, the parameters are adjusted to increase the buffering capacity in the interval of interest.

When a satisfactory buffer composition is selected, the weight of buffer required is calculated by converting the millequivalent buffer units of the calculation to the weight in grams by multiplying by the equivalent weight of the specific amino acid.

As indicated in the notes to the method, $pK_a$'s of buffering agents are quite sensitive to activity coefficients, and these should be determined or calculated at the final molar concentration of the buffer in the emulsion formulation. The $pK_a$ must also be that of the stable emulsion temperature if the computation is to be accurate.

When an optimal buffer is selected it may be empirically tested in the formulation by manual titration to verify the buffer capacity in the region of interest. Titrations in the region of neutrality, using dilute reagents, can safely be carried out without lipid degradation.

CALCULATION OF THE TITRATION CURVE FOR A POLYPROTIC SYSTEM; CALCULATION OF THE BUFFERING CAPACITY OF THE SYSTEM AS THE FIRST DERIVATIVE OF THE TITRATION CURVE

The following calculations are the basis of a computer program which calculates a titration curve, $cH_e$xt v. $cH^+$, for weak acids or bases in multiprotic systems such as amino acids. From the titration curve data, the buffering capacity of an amino acid buffer system at any pH can be readily determined as $dcH_{ext}/dpH$. The derivative is determined numerically.

A mathematical description of a titration curve for a weakly dissociated, multiprotic system can be derived by treating the system as an interrelated system of several weak acids (or bases). The model is histidine.

The calculations are based on the well-known Henderson-Hasselbach equation which is used to compute the pH of a buffer system from the ionization constant of a weak acid or base, as follows:

$$pH = pK_a + \log \frac{[Ac-]}{[HAc]}$$

When half of the acid has been converted to a salt by the addition of base (or the reverse process), the ratio of salt to acid is 1, the log of the ratio is 0, and pH=pK. pH is then a calculable function of added (or removed) $H^+$ ions, ($cH_{ext}$) and $H^+$ ions ($cH$), free in the buffered solution.

The buffering capacity can be defined as the amount of $H+$ ions a buffered solution can neutralize within the range of one pH unit, or $\Delta H^+/\Delta pH$. At the limit, the derivative $dH+/dpH$ is also identically the slope of the titration curve.

If we could derive an expression for this derivative, it could then be integrated between any pair of pH values to give the buffering capacity within that range directly.

In this algorithm we do not compute the derivative for the buffering capacity directly, although with some effort that could be done. As the calculations show, the relationship between $H+$ concentration and the various $K_a$'s of the titratable groups involve complex fractions. Specifically, rather than differentiating Eq. 5(a), it's much easier to compute the derivatives, $dcH_{ext}/dcH$ and $dcH/dpH$, whose product is $dH+/dPH$. This product reduces to one derivative which can be differentiated numerically, $[f(x+dx)-f(x)/dx]$, and that's what the computer program does, using a dpH of 0.0001.

BUFFERING CAPACITY OF A TRIPROTIC AMINO ACID

Basis of the Calculations

1. Henderson-Hasselbach Equations $$cA^+ \; cH^+ = K_1 cA^{++} \; K_1 = 10^{-1.82}$$

$$cA^0 \; cH^+ = K_2 cA^+ \; K_2 = 10^{-6.00}$$

$$cA^- \; cH^+ = K_3 cA^0 \; K_3 = 10^{-9.17}$$

2. Conservation of A (the amino acid)

$$cA^{++} + cA^+ + cA^0 + cA^{-1} = M$$

3. Conservation of $H^+$ $$cH^+ = cOH^- = (q-2)cA^{++} + (q-1)cA^+ + (q-)cA^0 + (q-1)cA^- + cH^+_{ext},$$

where $cH_{ext}$ is added $H^+$ (e.g., from HCl); and q is the original charge of the amino acid before dissociation.

4. Water dissociation $$cH^+ cOH^- = 55.6 \times 10^{-14}$$

5. Rate of change of $H^+$ with pH $$pH = -\log_{10}(cH^+)$$

$$cH^+ = 10^{-pH} = e^{-\ln 10 \times pH}$$

$$dcH^+/dpH = -\ln 10 \times 10^{pH} = -\ln 10 \times cH^+$$

Solutions: by Gaussian Eliminaton
By (1):

$$cA^0 = \frac{cH}{K_3} cA^-$$

$$cA^+ = \frac{cH}{K_2} cA^0 = \frac{cH}{K_2} \frac{cH}{K_3} cA^-$$

$$cA^{++} = \frac{cH}{K_1} cA^+ = \frac{cH}{K_1} \frac{cH}{K_2} \frac{cH}{K_0} cA^-$$

By (2):

$$\frac{cH}{K_1} \frac{cH}{K_2} \frac{cH}{K_3} cA^- +$$

$$\frac{cH}{K_2} \frac{cH}{K_3} cA^- + \frac{cH}{K_3} cA^- + cA^- = M$$

Thus, $$A = \frac{M}{\frac{cH}{K_1} \frac{cH}{K_2} \frac{cH}{K_3} + \frac{cH}{K_2} \frac{cH}{K_3} + \frac{cH}{K_3} + 1}$$

$$= \frac{M}{\frac{cH}{K_1} + 1 \frac{cH}{K_2} + 1 \frac{cH}{K_3} + 1}$$

Computation:

1. $cA^- = \dfrac{M}{\frac{cH}{K_1} + 1 \frac{cH}{K_2} + 1 \frac{cH}{K_3} + 1}$

2. $cA^0 = \dfrac{cH}{K_3} cA^-$

3. $cA^+ = \dfrac{cH^+}{K_2} cA^0$

4. $cA^{++} = \dfrac{cH^+}{K^1} cA^+$

The Titration Curve:

5. $cH_{ext} = cH^+ - \dfrac{K_w}{cH^+} + 2cA^{++} + cA^+ - A^+ - cA^- - qM$ (If only $cH_{ext}$ vs. cH is needed and not the several cA's, this can be expressed as:)

$$cH_{ext} = cH - \frac{K_w}{cH} + \frac{2\frac{cH}{K_1} + 1\frac{cH}{K_2}\frac{cH}{K_3} - 1}{\frac{cH}{K_1} + 1\frac{cH}{K_2} + 1\frac{cH}{K_3} + 1} - M - qM$$

Buffering Capacity =

$$\frac{dcH_{ext}}{dpH} = \frac{dcH_{ext}}{dcH} \frac{dcH}{dpH} = -\ln 10 \times \frac{dcH_{ext}}{dcH}$$

(Note buffering capacity does not depend on q)

The program for two buffering agents was easily written by modifying the basic program of Example 2.

To include a second amino acid (as was done for methyl histidine), the calculations were modified by writing:

a. New H-H equations $$cB^- cH^+ = K\, cB^0 \text{ etc.} \quad \text{(Eq. 1)}$$

b. An expression for the conservation of species B $$cB^- + cB^0 \ldots = Mq \quad \text{(Eq. 2)}$$

c. The expression for the conservation of H+ (Eq.3) to add more terms for B, B+...

Then, we obtained parallel solutions for the $cB^x$'s, and included the cBx values in the equation for conservation of H+ (Eq.5).

The result for the titration curve expression, Eq.5, was modified by adding fractions for the second species. Similar modifications are made to calculate the capacity of buffers having additional species. See the terms for the cB's and $cH_{ext}$ in the programs for histidine, the mixture of histidine and methyl histidine, and the mixture of histidine and imidazole.

The accuracy of the calculations depend largely on the choice of correct values of the $K_a$'s or $K_b$'s. These values first of all have a temperature dependence. They can be found in some handbooks for various standard temperatures, or one can calculate them from the van't Hoff equation, (K proportional to exp dH/RT). The more important warning is that the crucial variables in the dissociation equations are not the concentrations, but the activities. Activities are concentration and "ionic strength" dependent (see the Debye-Huckel Equation). pK's vary by ± a few tenths because of this and there are similar variations due to temperature. For that reason, optimal buffer formulations as predicted by the program, should be empirically verified before their use in the emulsion products.

In the Pascal program: "Calc Equilib" takes pH as an input, and returns (var) the values for $cA^{-1}$, $cA^0$, $cA^{+1}$, $cA^{+2}$ and $cH_{ext}$ (the various ionic concentrations). To use the programs of Examples 3 through 5, one need only input the Ka's of each constituent amino acid and its concentration in milliequivalents.

All the ionizable groups are determined, even when their values are insignificant. It is easier to do this in numerical work, rather than ignoring them or letting them go to zero, as in hand calculations, or textbook approximations.

Figure 1B:
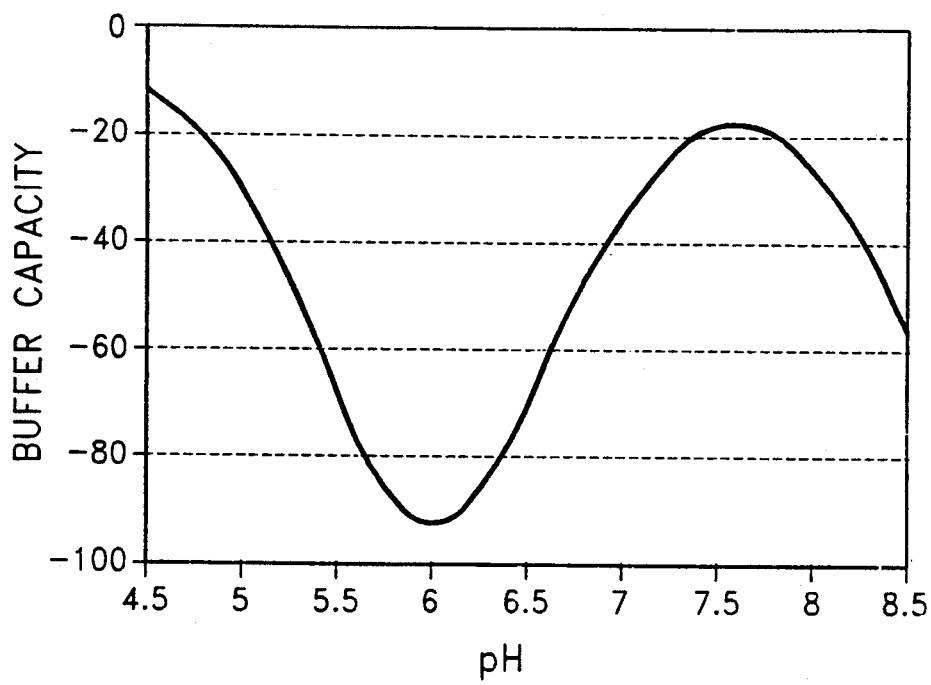
FIG. 1b is a graph of the titration of histidine buffer capacity.

In Example 5, the first program, we determine the buffering capacity of histidine at a concentration of 0.161M (161 milliequivalents, (meq) corresponding to the manual titration of Kresh, above). The $pK_a$'s used for histidine are: 1.82 (COOH); 6.00 (imidazole N); 9.17 (NH$_2$). The results of the calculations are graphed as titration curve FIG. 1A and a buffering capacity curve FIG. 1B between the pH values 4.5 and 8.5.

Next, in Example 6, the same calculations are carried out for a mixture of 80 meq each of 0.08 milliequivalents each of histidine and imidazole, wherein the pK chosen for the single ionizable group of imidazole is 6.99. The program of the example calculates the titration of a buffer system having six ionizable groups, for example two triprotic amino acids, according to expressions developed above for a two amino acid system. The pK values for histidine are assigned as in the above example, and the $pK_a$ for imidazole is assigned to Kb3. Kb1 and Kb2 are turned off. A buffering capacity curve for the mixture is plotted from the calculated data and presented in FIG. 2.

In Example 5, the program is adapted to determine the titration of a mixture of 80 meq each of histidine and methyl histidine. The pK's of the methyl derivative are shifted to 5.01 and 7.23 and these values are assigned to the constants Kb2 and Kb3 of the program described for Example 6. The buffering capacity curve is presented in FIG. 3. Numerical data from the calculations of all cases is presented in corresponding Tables I, II and III.

A comparison of FIGS. 1, 2 and 3 indicates the difference in buffering capacity of the three systems. Since all systems have the same total number of milliequivalents, the total buffering capacity over the complete pH range is identical. However, by using mixtures of amino acids, one is able to concentrate that buffering capacity within a range of interest. Note that the buffering capacity of histidine is concentrated between 5.5 and 6.5, within ±0.05 units of a $pK_a$, the normal region of greatest buffering capacity. Only the region between from about 5.2 to 6.9 has a buffer capacity greater than 40 meq/pH. Using a mixture of histidine and imidazole, the buffering capacity is shifted and broadened, and the capacity is greater than 40 meq/pH from 5.5 to 7.5. In the case of a mixture of histidine and methyl histidine buffers, the buffer capacity is spread out over the entire pH interval plotted, and the buffering capacity is above 40 meq/pH from pH 4.5 to 7.8. The mixed buffer systems are also more efficient. Note that to change the pH of the buffered solution containing 161 meq of histidiine from 7.6 to 7.2 requires only 0.1665−0.1607=5.8 meq of H+; the same change between the same points in a buffer containing 80 meq His and 80 meq Methyl His requires 0.0608−0.0402=20.6 meq of H+; the same change in a buffer of 80 meq His and 80 meq Imid requires 17.8 meq. These values are computed from the values of the $CH_{ext}$ at the two pH's.

Buffering capacity is directly related to the concentration of the buffering species. Since amino acids are physiologically innocuous and well tolerated, substantial concentrations may be used to achieve the required buffering effect. In preferred embodiments, therefore, the concentration of buffering amino acids in the fluorocarbon emulsions is form 0.01M to 0.5M; and in particularly preferred embodiments, from 0.01M to 0.2M.

By means of applying this method of calculation to various combinations of amino acids in various relative concentrations, the most efficient amino acid buffer, in terms of its capacity to resist pH changes, can be selected for a given pH range and a fixed total amino acid concentration.

The combinations of amino acid derived structures whose amphoteric properties can be exploited to buffer fluorocarbon emulsions are virtually unlimited. The use of not only native amino acids, but their substituted forms, such as, for example, the methyl esters and amides of amino groups, either alone or in combination with the parent molecules, provides a selection of buffering agents having fine gradations in buffering capacity at a selected pH. For example, the methyl ester of histidine shifts the $pK_2$ (imidazolyl) of native histidine from 6.00 to 7.23; the same pK pf histidine amide is at 7.64 (25° C.).

Combining amino acids into small oligopeptides also shifts the pK's of constituent amphoteric groups. For example, the same reference pK of native histidine shifts to 6.80 in histidylhistidine, and to 5.80 in histidylglycine. Natural dipeptide buffers, such as carnosine (N-β-alanyl-L-histidine) and anserine (N-β-alanyl-3-methyl-L-histidine), whose physiological buffering action is described by Parkhouse, W. et al. *J. Appl. Physiol.* 58(1):14–17 (1985), can be usefully combined with other buffers to achieve optimum buffering capacity in the present invention. The peptide binding of histidine with other amino acids shifts its low $pK_2$ into a higher range where it becomes more useful as a physiological buffer.

A more complete understanding of the invention can be obtained by referring to the following illustrative examples which are not intended, however, to unduly limit the invention.

EXAMPLE 1

Anti-Pyretic Effect of Imidazole Containing Fluorocarbon Emulsions in Tumor Bearing Subjects New Zealand white rabbits were given intrahepatic inoculations of VX-2 tumor cells. After a period of 18 days, to allow for tumor growth, the rabbits were submitted to a pyrogenicity test using the protocol described on pp.1181-2 of the United States Pharmacopeia, 21st Ed. 1985. Briefly, this test consisted of measuring rectal temperature every 15–30 minutes over a 3 hour period after an intravenous injection of 10 Ml/kg of a 100% w/v emulsion of perfluorooctylbromide in which the emulsifying agent was egg yolk phospholipid in a concentration of 4.5% w/v. A rabbit is considered to pass the test when the rectal temperature does not exceed 0.5° C. above the baseline temperature. The emulsion formulations were as follows:

| 1) Tromethamine buffered | |
|---|---|
| PFOB | 100% W/V |
| Egg yolk phospholipid | 4.5% |
| Mannitol | 0.4% |
| NACl | 0.25% |
| d-alpha tocopheryl acetate | 0.05% |
| $NA_2CA$ EDTA | 0.04% |
| Tromethamine | 0.1% |
| $H_2O$ | q.s. |
| 2) Imidazole-histidine buffered | |
| PFOB | 100% W/V |
| Egg yolk phospholipid | 4.5% |
| Mannitol | 0.4% |
| NACl | 0.25% |
| d-alpha tocopheryl acetate | 0.05% |
| $NA_2CA$ EDTA | 0.04% |
| Imidazole | 0.1% to 0.3% |
| Histidine | 0.1% |
| $H_2O$ | q.s. |

The results of the tests were as follows:
1) 3 out of 9 rabbits passed after receiving the 0.5% tromethamine buffered emulsion.
2) 9 out of 11 rabbits passed after receiving the emulsion buffered with 0.1% imidazole plus 0.1% histidine.

It appears that imidazole is the pharmacologically effective antipyretic agent since ¾ of the rabbits passed after receiving an emulsion containing 0.1% imidazole alone and 0/2 passed after receiving an emulsion containing 0.1% histidine as the only buffer. Although histidine contains an imidazole ring, this component is chemically bound to the pyridine part of the molecule. The histidine is used in this emulsion to increase the buffer capacity.

D-alpha tocopherol acetate in a concentration of 0.05% works synergistically with these buffers since 1/6 rabbits passed the test when tocopherol was deleted from the imidazole-histidine buffered emulsion and 6/17 rabbits passed when d-alpha tocopherol was deleted from the tromethamine buffered emulsion.

EXAMPLE 2

Anti-Pyretic Effect of Buffer Composition and Imidazole Concentration in Standard Formulations of 100% PFOB Emulsions Using the protocol of Example 1, but varying the buffer compositions of the 100% PFOB formulations described therein as indicated in the table below, the anti-pyretic effect of imidazole was determined as follows:

| Buffer System | Pyrogenic/Total Response | |
|---|---|---|
| | Number | Percent |
| 0.1% Tham | 6/24 | 25% |
| 0.1% Hist; 0.1% Imid | 2/11 | 18.2% |
| (without tocopherol) | (3/3) | (100.0%) |
| 0.1% Hist; 0.2% Imid | 1/10 | 10% |
| 0.1% Hist; 0.3% Imid | 1/9 | 11% |

EXAMPLE 3

Frequency of Pyrogenic Response to PFOB Emulsions In Healthy and Tumor-Bearing Rabbits Tham Buffer versus Imidazole+Histidine Buffer

| | Healthy | | Tumor | | |
|---|---|---|---|---|---|
| 0.1% Tham | 98.2% | 54/55 | 75% | 18/24 | p = 0.003 |
| 0.1 to 0.3% Imidazole + 0.1% Histidine | 96.2% | 25/26 | 88.5% | 23/26 | N.S. |

The rabbits received 10 mL/kg intravenously of a 100% w/v PFOB emulsion and rectal temperature was measured for three hours using the protocol for the Pyrogen Test as described in Example 1.

EXAMPLE 4

Comparison of Statistically Significantly Different Blood Values In Rats Receiving Tham and Imidazole and Histidine-Buffered Emulsions

| | 0.1% Tham | 0.3% Imidazole + 0.1% Histidine | P value |
|---|---|---|---|
| Glucose ↓ | 143 ± 4.2 | 162.8 ± 2.3 | <0.01 |
| Alkaline Phosphatase | 322 ± 2.7 | 258.5 ± 10.8 | <0.05 |
| Phosphorus | 10.2 ± 0.1 | 9.6 ± 0.2 | <0.05 |
| Potassium | 5.4 ± 0.1 | 4.5 ± 0.1 | <0.001 |
| Chloride | 106 ± 0.6 | 104.2 ± 0.4 | <0.05 |
| Cholesterol | 109 ± 3.6 | 97 ± 3.6 | <0.05 |
| Calcium | 9.9 ± 0.1 | 9.4 ± 0.1 | <0.01 |
| Globulin ↓ | 1.7 ± 0.03 | 2.0 ± 0.04 | <0.001 |
| Lactic Dehydrogenase | 1656 ± 91 | 1035 ± 90 | <0.001 |

|  | 0.1% Tham | 0.3% Imidazole + 0.1% Histidine | P value |
|---|---|---|---|
| White Blood Count | 3176 ± 22 | 4250 ± 90 | <0.01 |

Glucose, serum globulin and white blood counts decreased significantly in rats receiving Tham buffered emulsion. Alkaline phosphatase, potassium, chloride, phosphorus, cholesterol, calcium and lactic dehydrogenase elevated significantly in rats receiving Tham buffered emulsion compared with rats receiving emulsion buffered with 0.3% Imidazole plus 0.1% Histidine. There were six female rats in each group. Each received a dose of 4 mL/kg of 100% w/v PFOB emulsion (this emulsion contained about 1000 ppm PFOI) and were sacrificed one week later.

EXAMPLE 5

PROGRAM FOR HISTIDINE BUFFER

```
Const
  dpH = 0.0001;
  M = 0.161:
  q = -1;  {initial undissociated Histidine charge-state}
  Sep = ', ';
var
  Kw, Ka1, Ka2, Ka3 : real;
Procedure CalcEquilib (pH : real; var cAm1, cA0, cAp1,
cAp2, cHext : real); var
  cH : real;
begin
  cH := exp (-pH*ln (10));
  cAm1 := M/( ((cH/Ka1+1)*cH/Ka2+1)*cH/Ka3+1 );
  cA0 := cH*cAm1/Ka3;
  cAp1 := cH*cA0/Ka2;
  cAp2 := cH*cAp1/Ka1;
  cHext := cH - Kw/cH + 2*cAp2 + cAp1 - cAm1 - q*M;
end;
function BufCap (pH : real) : real;
var
```

PROGRAM FOR HISTIDINE BUFFER

```
  c1, c2, x, y, z, t : real;
begin
  CalcEquilib(pH + dpH, x,y,z,t, c1);
  CalcEquilib(pH,       x,y,z,t, c2);
  BufCap := 1000*(c1 -c2)/dpH
end;
Const
  pHStep = 0.1;
var
  j : integer;
  pH, cAm1, cA0, cAp1, cAp2, cHext : real;
begin
  Kw := (1000/18)*1.0e-14;
  Ka1 := exp(-1.82*ln(10));  { 1-COOH }
  Ka2 := exp(-6.0*ln(10));   { 2-NH2 }
  Ka3 := exp(-9.17*ln(10));  { 1-NH2 }
  pH := 2.5;
  writeln('      Histidine buffer, ', 1000*M:0:0, '  mEq');
  writeln
  pH    cAm1    cA0    cAp1    cAp2    cHext    BufCap'
  );
  for j := 0 to 80 do begin
  CalcEquilib(pH, cAm1, cA0, cAp1, cAp2, cHext);
  writeln( pH:4:1, Sep,
           cAm1 : 10:8, Sep,
           cA0: 10:8, Sep,
           cAp1: 10:8, Sep,
           cAp2: 10:8, Sep,
           cHext: 6:4, Sep,
           BufCap(pH): 6:1);
  pH := pH + pHStep;
  end;
end.
```

EXAMPLE 5

Program for Histidine-Imidazole Buffer

```
Const
  dpH = 0.0001;
  Ma = 0.08; {80 meq}
  Mb = 0.08; { " }
  q = 0;   {initial undissociated Histidine charge-state}
  Sep = ', ';
var
  Kw, Ka1, Ka2, Ka3, Kb1, Kb2, Kb3 : real;
procedure CalcEquilib(pH : real;
                  var cAm1, cA0, cAp1, cAp2,
                      cBm1, cB0, cBp1, cBp2,
                      cHext : real);
var
  cH : real;
begin
  cH :=exp(-pH*ln(10));
  cAm1 := Ma/( ((cH/Ka1+1)*cH/Ka2+1)*cH/Ka3+1 );
  cA0 := cH*cAmi/Ka3
  cAp1 :=cH*cA0/Ka2
  cAp2 :=cH*cAp1/Ka1
  cBm1 :=Mb/( ((cH/Kb1+1)*cH/Kb2+1)*cH/Kb3+1 );
  cB0 :=cH*cBm1/Kb3;
  cBp1 := cH*cB0/Kb2;
  cBp2 := cH*cBp1/Kb1;
  cHext := Ch - Kw/cH + 2*cAp2 + cAp1 - cAm1 + 2*cBp2 + cBp1
  - cBm1; end;
function BufCap (pH : real) : real:
var
  c1,c2, x, y, z, t, p, q, r, s : real;
begin
  CalcEquilib(pH + dpH, x,y,z,t,p,q,r,s, c1);
  CalcEquilib(pH,       x,y,z,t,p,q,r,s, c2);
  BufCap := 1000*(c1 - c2)/dpH
```

-continued

Program for Histidine-Imidazole Buffer

```
end;
const
  pHstep = 0.1;
var
  j : integer;
  pH, cAm1, cAo, cAp1, cAp2, cHext : real;
  x, y, z, t : real;
begin
  Kw := (1000/18)*1.0e-14;
  Ka1 := exp(-1.82*ln(10));    {1-COOH}
  Ka2 := exp(-6.0*ln(10));     {1-NH2}
  Ka3 := exp(-9.17*ln(10));    {5-NH2}
  Kb1 := exp(10);      {only one charge state -- turn these off}
  Kb2 := exp(10);
  Kb3 := exp(-6.99*ln(10));
  pH := 2.5;
  write('       Histidine: ', 1000*Ma:0:0, ', mEq');
  writeln('   Imidazole: ', 1000*Mb:0:0, ', mEq');
  ' pH     cAm1      cA0       cAp1      cAp2      cHext
BufCap'
        );
  for j := 0 to 80 begin
        CalcEquilib(pH, cAm1, cA0, cAp1, cAp2, x,y,z,t,
cHext);
        writeln( pH:4.1, Sep,
                 cAm1:10:8, Sep,
                 cA0:10:8, Sep,
                 cAp1:10:8, Sep,
                 cAp2:10:8, Sep,
                 cHext:6:4, Sep,
                 BufCap(pH):6:1);
        pH := pH + pHStep
        end;
end.
```

EXAMPLE 6

Program for Histidine and Methyl Histidine Buffer

```
Const
  dpH = 0.0001;
  Ma = 0.08;   {80 meq}
  Mb = 0.08;   {80 meq}
  q = 0;       (initial undissociated Histidine charge-state)
  Sep = ', ';
var
  Kw, Ka1, Ka2, Ka3, Kb1, Kb2, Kb3 : real;
  procedure CalcEquilib(pH : real;
                   var cAm1, cA0, cAp1, cAp2,
                       cBm1, cB0, cBp1, cBp2,
                       cHext : real);
var
  cH : real;
begin
  cH := exp(-pH*ln(10));
  cAm1 := Ma/( ((cH/Ka1+1)*cH/Ka2+1)*cH/Ka3+1 );
  cA0 := cH*cAm1/Ka3;
  cAp1 := cH*cA0/Ka2;
  cAp2 := cH*cAp1/Ka1;
  cBm1 := Mb/( ((cH/Kb1+1)*cH/Kb2+1)*cH/Kb3+1 );
  cB0 := cH*cBm1/Kb3;
  cBp1 := cH*cB0/Kb2;
  cBp2 := cH*cBp1/Kb1;
  cHext := Ch - Kw/cH + 2*cAp2 + cAp1 - cAm1 + 2*cBp2 + cBp1
- cBm1; end;
function BufCap (pH : real) : real;
var
  c1,c2, x, 7, z, t, p, q, r, s : real;
begin
  CalcEquilib(pH + dpH, x,y,z,t,p,q,r,s, c1);
  CalcEquilib(pH,       x,y,z,t,p,q,r,s, c2);
  BufCap := 1000*(c1 - c2)/dpH
end;
const
  pHstep = 0.1;
var
  j : integer;
```

-continued

Program for Histidine and Methyl Histidine Buffer

```
    pH, cAm1, cAo, cAp1, cAp2, cHext : real;
    x, y, z, t : real;
begin
    Kw := (1000/18)*1.0e-14;
    Ka1 := exp(-1.82*ln(10));    {1-COOH}
    Ka2 := exp(-6.0*ln(10));     {1-NH2}
    Ka3 := exp(-9.17*ln(10));    (5-NH2}
    Kb1 := exp(10);  {only two charge states -- turn this one off}
    Kb2 := exp(-5.01*ln(10));
    Kb3 := exp(-7.23*ln(10));
    pH := 2.5;
    write('     Histidine: ', 1000*Ma:0:0, ,mEq');
    writeln(' Methyl Histidine: ' 1000*Mb:0:0, ' mEq');
'   pH       cAm1      cA0       cAp1      cAp2      cHext
BufCap'
        );
    for j := 0 to 80 do begin
        CalcEquilib(pH, cAm1, cAo, cAp1, cAp2, x,y,z,t,
cHext);
        writeln( pH:4.1, Sep,
                cAm1:10:8, Sep,
                cA0:10:8, Sep,
                cAp1:10:8, Sep,
                cAp2:10:8, Sep,
                cHext:6:4, Sep,
                BufCap(pH):6:1);
        pH := pH + pHStep
    end;
end.
```

Accordingly, the invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced with their scope.

TABLE 1

Titration of Histidine
161 milliequivalents (meq) of His; concentrations of cAm1; cAo; cAp1; cAp2; and cHext in meq; buffering capacity, Buf Cap, in meq/pH.

| pH | cAm1 | cA0 | cAp1 | cAp2 | cHext | BufCap |
|---|---|---|---|---|---|---|
| 2.5, | 0.00000000, | 0.00004210, | 0.13314083, | 0.02781706, | 0.3529, | −60.4 |
| 2.6, | 0.00000000, | 0.00005495, | 0.13803666, | 0.02290838, | 0.3474, | −51.2 |
| 2.7, | 0.00000000, | 0.00007126, | 0.14218509, | 0.01874365, | 0.3427, | −42.9 |
| 2.8, | 0.00000000, | 0.00009190, | 0.14565604, | 0.01525206, | 0.3387, | −35.7 |
| 2.9, | 0.00000000, | 0.00011798, | 0.14852800, | 0.01235402, | 0.3355, | −29.5 |
| 3.0, | 0.00000000, | 0.00015088, | 0.15088054, | 0.00996858, | 0.3328, | −24.2 |
| 3.1, | 0.00000000, | 0.00019235, | 0.15278916, | 0.00801849, | 0.3306, | −19.9 |
| 3.2, | 0.00000000, | 0.00024458, | 0.15432220, | 0.00643322, | 0.3288, | −16.3 |
| 3.3, | 0.00000000, | 0.00031034, | 0.15553927, | 0.00515039, | 0.3273, | −13.4 |
| 3.4, | 0.00000000, | 0.00039309, | 0.15649079, | 0.00411613, | 0.3261, | −11.1 |
| 3.5, | 0.00000000, | 0.00049717, | 0.15721808, | 0.00328475, | 0.3251, | −9.3 |
| 3.6, | 0.00000000, | 0.00062803, | 0.15775391, | 0.00261806, | 0.3242, | −8.0 |
| 3.7, | 0.00000000, | 0.00079249, | 0.15812304, | 0.00208447, | 0.3235, | −7.1 |
| 3.8, | 0.00000000, | 0.00099908, | 0.00165805, | 0.00165805, | 0.3228, | −6.5 |
| 3.9, | 0.00000001, | 0.00125841, | 0.15842388, | 0.00131771, | 0.3222, | −6.2 |
| 4.0, | 0.00000001, | 0.00158370, | 0.15836995, | 0.00104364, | 0.3216, | −6.3 |
| 4.1, | 0.00000002, | 0.00199135, | 0.15817850, | 0.00083013, | 0.3209, | −6.7 |
| 4.2, | 0.00000003, | 0.00250160, | 0.15784038, | 0.00065799, | 0.3202, | −7.4 |
| 4.3, | 0.00000004, | 0.00313934, | 0.15733962, | 0.00052100, | 0.3194, | −8.4 |
| 4.4, | 0.00000007, | 0.00393494, | 0.15665295, | 0.00041204, | 0.3185, | −9.9 |
| 4.5, | 0.00000011, | 0.00492522, | 0.15574926, | 0.00032541, | 0.3174, | −11.9 |
| 4.6, | 0.00000017, | 0.00615430, | 0.15458898, | 0.00025655, | 0.3161, | −14.3 |
| 4.7, | 0.00000026, | 0.00767436, | 0.15312353, | 0.00020186, | 0.3145, | −17.4 |
| 4.8, | 0.00000041, | 0.00954607, | 0.15129509, | 0.00015843, | 0.3126, | −21.1 |
| 4.9, | 0.00000064, | 0.01183843, | 0.14903697, | 0.00012396, | 0.3103, | −25.6 |
| 5.0, | 0.00000099, | 0.01462749, | 0.14627488, | 0.00009664, | 0.3075, | −30.9 |
| 5.1, | 0.00000153, | 0.01799378, | 0.14292968, | 0.00007501, | 0.3041, | −37.0 |
| 5.2, | 0.00000236, | 0.02201766, | 0.13892206, | 0.00005791, | 0.3000, | −44.0 |
| 5.3, | 0.00000361, | 0.02677235, | 0.13417961, | 0.00004443, | 0.2953, | −51.6 |
| 5.4, | 0.00000549, | 0.03231447, | 0.12864621, | 0.00003384, | 0.2897, | −59.6 |
| 5.5, | 0.00000827, | 0.03867262, | 0.12229356, | 0.00002555, | 0.2833, | −67.8 |
| 5.6, | 0.00001234, | 0.04583535, | 0.11513320, | 0.00001911, | 0.2762, | −75.7 |
| 5.7, | 0.00001821, | 0.05374075, | 0.10722690, | 0.00001414, | 0.2882, | −82.6 |
| 5.8, | 0.00002656, | 0.06227070, | 0.09869240, | 0.00001033, | 0.2597, | −88.1 |
| 5.9, | 0.00003826, | 0.07125258, | 0.08970169, | 0.00000746, | 0.2507, | −91.7 |

TABLE 1-continued

Titration of Histidine
161 milliequivalents (meq) of His; concentrations of cAm1;
cAo; cAp1; cAp2; and cHext in meq; buffering capacity, Buf
Cap, in meq/pH.

| pH | cAm1 | cA0 | cAp1 | cAp2 | cHext | BufCap |
|---|---|---|---|---|---|---|
| 6.0, | 0.00005440, | 0.08047014, | 0.08047014, | 0.00000532, | 0.0214, | −93.0 |
| 6.1, | 0.00007633, | 0.08968255, | 0.07123738, | 0.00000374, | 0.2322, | −91.8 |
| 6.2, | 0.00010570, | 0.09864863, | 0.06224308, | 0.00000259, | 0.2231, | −88.4 |
| 6.3, | 0.00014454, | 0.10715098, | 0.05370270, | 0.00000178, | 0.2146, | −83.0 |
| 6.4, | 0.00019532, | 0.11501513, | 0.04578835, | 0.00000120, | 0.2066, | −76.2 |
| 6.5, | 0.00026109, | 0.12212028, | 0.03861782, | 0.00000081, | 0.1994, | −68.5 |
| 6.6, | 0.00034560, | 0.12840100, | 0.03225287, | 0.00000054, | 0.1929, | −60.5 |
| 6.7, | 0.00045351, | 0.13384129, | 0.02670485, | 0.00000035, | 0.1872, | −52.7 |
| 6.8, | 0.00059066, | 0.13846404, | 0.02194507, | 0.00000023, | 0.1824, | −45.4 |
| 6.9, | 0.00076430, | 0.14231869, | 0.01791686, | 0.00000015, | 0.1781, | −38.8 |
| 7.0, | 0.00098349, | 0.14546946, | 0.01454695, | 0.00000010, | 0.1746, | −33.1 |
| 7.1, | 0.00125956, | 0.14798547, | 0.01175490, | 0.00000006, | 0.1715, | −28.4 |
| 7.2, | 0.00160656, | 0.14993325, | 0.00946015, | 0.00000004, | 0.1688, | −24.6 |
| 7.3, | 0.00204195, | 0.15137148, | 0.00758655, | 0.00000003, | 0.1665, | −21.8 |
| 7.4, | 0.00258723, | 0.15234768, | 0.00606507, | 0.00000002, | 0.1645, | −19.8 |
| 7.5, | 0.00326886, | 0.15289613, | 0.00483500, | 0.00000001, | 0.1625, | −18.7 |
| 7.6, | 0.00411904, | 0.15303684, | 0.00384411, | 0.00000001, | 0.1607, | −18.4 |
| 7.7, | 0.00517669, | 0.15277504, | 0.00304826, | 0.00000000, | 0.1588, | −18.9 |
| 7.8, | 0.00648832, | 0.15210104, | 0.00000000, | 0.00000000, | 0,1569, | −20.3 |
| 7.9, | 0.00810867, | 0.15099047, | 0.00190086, | 0.00000000, | 0.1547, | −22.6 |
| 8.0, | 0.01010101, | 0.14940494, | 0.00149405, | 0.00000000, | 0.1523, | −25.8 |
| 8.1, | 0.01253669, | 0.14729331, | 0.00116999, | 0.00000000, | 0.1496, | −29.9 |
| 8.2, | 0.01549354, | 0.14459413, | 0.00091233, | 0.00000000, | 0.1463, | −34.9 |
| 8.3, | 0.01905268, | 0.14123945, | 0.00070787, | 0.00000000, | 0.1463, | −40.9 |
| 8.4, | 0.02329323, | 0.13716072, | 0.00054605, | 0.00000000, | 0.1381, | −47.8 |
| 8.5, | 0.02828460, | 0.13229704, | 0.00041836, | 0.00000000, | 0.1330, | −55.4 |
| 8.6, | 0.03407635, | 0.12660563, | 0.00031802, | 0.00000000, | 0.1270, | −63.4 |
| 8.7, | 0.04068639, | 0.12007404, | 0.00023958, | 0.00000000, | 0.1203, | −71.5 |
| 8.8, | 0.04808921, | 0.11273212, | 0.00017867, | 0.00000000, | 0.1127, | −79.1 |
| 8.9, | 0.05620662, | 0.10466162, | 0.00013176, | 0.00000000, | 0.1045, | −85.8 |
| 9.0, | 0.06490398, | 0.09600002, | 0.00009600, | 0.00000000, | 0.0956, | −90.9 |
| 9.1, | 0.07399472, | 0.08693622, | 0.00006906, | 0.00000000, | 0.0864, | −94.0 |
| 9.2, | 0.08325391, | 0.07769707, | 0.00004902, | 0.00000000, | 0.0769, | −94.8 |
| 9.3, | 0.09243939, | 0.06852627, | 0.00003434, | 0.00000000, | 0.0675, | −93.4 |
| 9.4, | 0.10131661, | 0.05965964, | 0.00002375, | 0.00000000, | 0.0583, | −89.8 |
| 9.5, | 0.10968176, | 0.05130201, | 0.00001622, | 0.00000000, | 0.0496, | −84.6 |
| 9.6, | 0.11737872, | 0.04361033, | 0.00001095, | 0.00000000, | 0.0414, | −78.4 |
| 9.7, | 0.12430706, | 0.03668562, | 0.00000732, | 0.00000000, | 0.0339, | −71.7 |
| 9.8, | 0.13042140, | 0.03057376, | 0.00000485, | 0.00000000, | 0.0271, | −65.1 |
| 9.9, | 0.13572385, | 0.02527296, | 0.00000318, | 0.00000000, | 0.0209, | −59.2 |
| 10.0, | 0.14025299, | 0.02074494, | 0.00000207, | 0.00000000, | 0.0152, | −54.4 |
| 10.1, | 0.14407171, | 0.01692695, | 0.00000134, | 0.00000000, | 0.0099, | −51.0 |
| 10.2, | 0.14725637, | 0.01374276, | 0.00000087, | 0.00000000, | 0.0049, | −49.2 |
| 10.3, | 0.14988809, | 0.01111136, | 0.00000056, | 0.00000000, | 0.0000, | −49.3 |
| 10.4, | 0.15204648, | 0.00895316, | 0.00000036, | 0.00000000, | −0.0050, | −51.6 |
| 10.5, | 0.15380574, | 0.00719403, | 0.00000023, | 0.00000000, | −0.0104, | −56.3 |

TABLE II

Titration of Histidine and Imidazole Mixture
80 milliequivalents (meq) each of His and Imid;
concentrations of cAm1; cAo; cAp1; cAp2; and cHext in meq;
buffering capacity, Buf Cap, in meq/pH.

| pH | cAm1 | cA0 | cAp1 | cAp2 | cHext | BufCap |
|---|---|---|---|---|---|---|
| 2.5, | 0.00000000, | 0.00002092, | 0.06615694, | 0.01382214, | 0.0970, | −33 |
| 2.6, | 0.00000000, | 0.00002731, | 0.06858965, | 0.01138305, | 0.0939, | −28 |
| 2.7, | 0.00000000, | 0.00003541, | 0.07065098, | 0.00931361, | 0.0913, | −23 |
| 2.8, | 0.00000000, | 0.00004567, | 0.07237567, | 0.00757866, | 0.0891, | −19 |
| 2.9, | 0.00000000, | 0.00005862, | 0.07380273, | 0.00613864, | 0.0873, | −16 |
| 3.0, | 0.00000000, | 0.00007497, | 0.07497170, | 0.00495333, | 0.0859, | −13.2 |
| 3.1, | 0.00000000, | 0.00009558, | 0.07592008, | 0.00398434, | 0.0847, | −10.8 |
| 3.2, | 0.00000000, | 0.00012153, | 0.07668184, | 0.00319663, | 0.0837, | −8.9 |
| 3.3, | 0.00000000, | 0.00015421, | 0.07728659, | 0.00255920, | 0.0829, | −7.3 |
| 3.4, | 0.00000000, | 0.00019532, | 0.07775940, | 0.00204528, | 0.0822. | −6.0 |
| 3.5, | 0.00000000, | 0.00024704, | 0.07812079, | 0.00163217, | 0.0817, | −5.1 |
| 3.6, | 0.00000000, | 0.00031206, | 0.07838703, | 0.00130090, | 0.0812, | −4.3 |
| 3.7, | 0.00000000, | 0.00039379, | 0.07857045, | 0.00103576, | 0.0808, | −3.8 |
| 3.8, | 0.00000000, | 0.00049644, | 0.07867969, | 0.00082388, | 0.0804, | −3.5 |
| 3.9, | 0.00000000, | 0.00062529, | 0.07871994, | 0.00065476, | 0.0801, | −3.4 |
| 4.0, | 0.00000001, | 0.00078693, | 0.07869314, | 0.00051992, | 0.0798, | −3.4 |
| 4.1, | 0.00000001, | 0.00098949, | 0.07859801, | 0.00041249, | 0.0794, | −3.6 |
| 4.2, | 0.00000001, | 0.00124303, | 0.07843000, | 0.00032695, | 0.0790, | −4.0 |
| 4.3, | 0.00000002, | 0.00155992, | 0.07818118, | 0.00025888, | 0.0786, | −4.6 |
| 4.4, | 0.00000003, | 0.00195525, | 0.07783998, | 0.00020474, | 0.0781, | −5.4 |
| 4.5, | 0.00000005, | 0.00244732, | 0.07739094, | 0.00016169, | 0.0775, | −6.5 |

TABLE II-continued

Titration of Histidine and Imidazole Mixture
80 milliequivalents (meq) each of His and Imid;
concentrations of cAm1; cAo; cAp1; cAp2; and cHext in meq;
buffering capacity, Buf Cap, in meq/pH.

| pH | cAm1 | cA0 | cAp1 | cAp2 | cHext | BufCap |
|---|---|---|---|---|---|---|
| 4.6, | 0.00000008, | 0.00305804, | 0.07681440, | 0.00012748, | 0.0768, | −7.9 |
| 4.7, | 0.00000013, | 0.00381334, | 0.07608623, | 0.00010030, | 0.0759, | −9.6 |
| 4.8, | 0.00000020, | 0.00474339, | 0.07517769, | 0.00007872, | 0.0748, | −11.7 |
| 4.9, | 0.00000032, | 0.00588245, | 0.07405564, | 0.00006160, | 0.0735, | −14.2 |
| 5.0, | 0.00000049, | 0.00726832, | 0.07268317, | 0.00004802, | 0.0720, | −17.2 |
| 5.1, | 0.00000076, | 0.00894101, | 0.07102096, | 0.00003727, | 0.0701, | −20.7 |
| 5.2, | 0.00000117, | 0.01094045, | 0.06902960, | 0.00002878, | 0.0678, | −24.7 |
| 5.3, | 0.00000179, | 0.01330303, | 0.06667310, | 0.00002208, | 0.0651, | −29.2 |
| 5.4, | 0.00000273, | 0.01605688, | 0.06392358, | 0.00001681, | 0.0620, | −34.1 |
| 5.5, | 0.00000411, | 0.01921621, | 0.06076699, | 0.00001270, | 0.0583, | −39.3 |
| 5.6, | 0.00000613, | 0.02277533, | 0.05720904, | 0.00000949, | 0.0541, | −44.5 |
| 5.7, | 0.00000905, | 0.02670348, | 0.05328045, | 0.00000702, | 0.0494, | −49.6 |
| 5.8, | 0.00001320, | 0.03094196, | 0.04903970, | 0.00000514, | 0.0442, | −54.3 |
| 5.9, | 0.00001901, | 0.03540501, | 0.04457227, | 0.00000371, | 0.0385, | −58.4 |
| 6.0, | 0.00002703, | 0.03998516, | 0.03998516, | 0.00000264, | 0.0325, | −61.7 |
| 6.1, | 0.00003793, | 0.04456276, | 0.03539746, | 0.00000186, | 0.0262, | −64.2 |
| 6.2, | 0.00005252, | 0.04901795, | 0.03092824, | 0.00000129, | 0.0197, | −66.0 |
| 6.3, | 0.00007182, | 0.05324272, | 0.02668457, | 0.00000088, | 0.0130, | −67.2 |
| 6.4, | 0.00009706, | 0.05715037, | 0.02275197, | 0.00000060, | 0.0063, | −67.8 |
| 6.5, | 0.00012973, | 0.06068088, | 0.01918898, | 0.00000040, | −0.0005, | −68.1 |
| 6.6, | 0.00017172, | 0.06380174, | 0.01602627, | 0.00000027, | −0.0073, | −68.0 |
| 6.7, | 0.00022535, | 0.06650499, | 0.01326949, | 0.00000017, | −0.0141, | −67.5 |
| 6.8, | 0.00029350, | 0.06880201, | 0.01090438, | 0.00000011, | −0.0208, | −66.5 |
| 6.9, | 0.00037977, | 0.07071736, | 0.00890279, | 0.00000007, | −0.0274, | −64.9 |
| 7.0, | 0.00048869, | 0.07228296, | 0.00722830, | 0.00000005, | −0.0337, | −62.5 |
| 7.1, | 0.00062587, | 0.07353315, | 0.00584095, | 0.00000003, | −0.0398, | −59.4 |
| 7.2, | 0.00079829, | 0.07450099, | 0.00470069, | 0.00000002, | −0.0456, | −55.7 |
| 7.3, | 0.00101463, | 0.07521564, | 0.00376971, | 0.00000001, | −0.0510, | −51.5 |
| 7.4, | 0.00128558, | 0.07570071, | 0.00301370, | 0.00000001, | −0.0559, | −47.0 |
| 7.5, | 0.00162428, | 0.07597323, | 0.00240248, | 0.00000001, | −0.0604, | −42.5 |
| 7.6, | 0.00204673, | 0.07604315, | 0.00191012, | 0.00000000, | −0.0644, | −38.3 |
| 7.7, | 0.00257227, | 0.07591306, | 0.00151466, | 0.00000000, | −0.0680, | −34.6 |
| 7.8, | 0.00322401, | 0.07557816, | 0.00119783, | 0.00000000, | −0.0713, | −31.5 |
| 7.9, | 0.00402915, | 0.07502632, | 0.00094453, | 0.00000000, | −0.0744, | −29.2 |
| 8.0, | 0.00501914, | 0.07423848, | 0.00074238, | 0.00000000, | −0.0772, | −27.8 |
| 8.1, | 0.00622941, | 0.07318922, | 0.00058136, | 0.00000000, | −0.0800, | −27.2 |
| 8.2, | 0.00769865, | 0.07184802, | 0.00045333, | 0.00000000, | −0.0827, | −27.5 |
| 8.3, | 0.00946717, | 0.07018109, | 0.00035174, | 0.00000000, | −0.0855, | −28.7 |
| 8.4, | 0.01157428, | 0.06815440, | 0.00027133, | 0.00000000, | −0.0884, | −30.6 |
| 8.5, | 0.01405446, | 0.06573766, | 0.00020788, | 0.00000000, | −0.0916, | −33.1 |
| 8.6, | 0.01693235, | 0.06290963, | 0.00015802, | 0.00000000, | −0.0951, | −36.1 |
| 8.7, | 0.02021684, | 0.05966412, | 0.00011905, | 0.00000000, | −0.0988, | −39.3 |
| 8.8, | 0.02389526, | 0.05601596, | 0.00008878, | 0.00000000, | −0.1029, | −42.5 |
| 8.9, | 0.02792875, | 0.05200577, | 0.00006547, | 0.00000000, | −0.1073, | −45.3 |
| 9.0, | 0.03225042, | 0.04770187, | 0.00004770, | 0.00000000, | −0.1120, | −47.6 |
| 9.1, | 0.03676756, | 0.04319812, | 0.00003431, | 0.00000000, | −0.1168, | −48.9 |
| 9.2, | 0.04136840, | 0.03860724, | 0.00002436, | 0.00000000, | −0.1217, | −49.3 |
| 9.3, | 0.04593262, | 0.03405032, | 0.00001707, | 0.00000000, | −0.1266, | −48.6 |
| 9.4, | 0.05034366, | 0.02964454, | 0.00001180, | 0.00000000, | −0.1314, | −47.0 |
| 9.5, | 0.05450025, | 0.02549168, | 0.00000806, | 0.00000000, | −0.1360, | −44.7 |
| 9.6, | 0.05832483, | 0.02166973, | 0.00000544, | 0.00000000, | −0.1403, | −42.0 |
| 9.7, | 0.06176749, | 0.01822888, | 0.00000364, | 0.00000000, | −0.1444, | −39.2 |
| 9.8, | 0.06480566, | 0.01519193, | 0.00000241, | 0.00000000, | −0.1482, | −36.7 |
| 9.9, | 0.06744042, | 0.01255799, | 0.00000158, | 0.00000000, | −0.1518, | −34.8 |
| 10.0, | 0.06969093, | 0.01030804, | 0.00000103, | 0.00000000, | −0.1552, | −33.7 |
| 10.1, | 0.07158843, | 0.00841091, | 0.00000067, | 0.00000000, | −0.1585, | −33.6 |
| 10.2, | 0.07317087, | 0.00682870, | 0.00000043, | 0.00000000, | −0.1619, | −34.8 |
| 10.3, | 0.07447855, | 0.00552117, | 0.00000028, | 0.00000000, | −0.1655, | −37.5 |
| 10.4, | 0.07555105, | 0.00444878, | 0.00000018, | 0.00000000, | −0.1695, | −41.9 |
| 10.5, | 0.07642521, | 0.00357468, | 0.00000011, | 0.00000000, | −0.1740, | −48.4 |

TABLE III

Titration of Histidine and Methyl Histidine
80 milliequivalents each of His and MetHis; concentrations
of cAm1; cAo; cAp1; cAp2; and $cH_{ext}$ in meq; buffering
capacity, Buf Cap, in meq/pH.

| pH | cAm1 | cA0 | cAp1 | cAp2 | cHext | BufCap |
|---|---|---|---|---|---|---|
| 2.5, | 0.00000000, | 0.00002092, | 0.06625694, | 0.01382214, | 0.1767, | −34.1 |
| 2.6, | 0.00000000, | 0.00002731, | 0.06858965, | 0.01138305, | 0.1736, | −29. |
| 2.7, | 0.00000000, | 0.00003541, | 0.07065098, | 0.00931361, | 0.1709, | −24.5 |
| 2.8, | 0.00000000, | 0.00004567, | 0.07237567, | 0.00757866, | 0.1686, | −20. |
| 2.9, | 0.00000000, | 0.00005862, | 0.07380273, | 0.00613864, | 0.1667, | −17.5 |
| 3.0, | 0.00000000, | 0.00007497, | 0.07497170, | 0.00495333, | 0.1651, | −15.6 |
| 3.1, | 0.00000000, | 0.00009558, | 0.07592008, | 0.00398434, | 0.1637, | −13.6 |

TABLE III-continued

Titration of Histidine and Methyl Histidine
80 milliequivalents each of His and MetHis; concentrations
of cAm1; cAo; cAp1; cAp2; and $cH_{ext}$ in meq; buffering
capacity, Buf Cap, in meq/pH.

| pH | cAm1 | cA0 | cAp1 | cAp2 | cHext | BufCap |
|---|---|---|---|---|---|---|
| 3.2, | 0.00000000, | 0.00012153, | 0.07668184, | 0.00319663, | 0.1625, | −11.6 |
| 3.3, | 0.00000000, | 0.00015421, | 0.07728659, | 0.00255920, | 0.1614, | −10.7 |
| 3.4, | 0.00000000, | 0.00019532, | 0.07775940, | 0.00204528, | 0.1603, | −10.3 |
| 3.5, | 0.00000000, | 0.00024704, | 0.07812079, | 0.00153217, | 0.1593, | −10.4 |
| 3.6, | 0.00000000, | 0.00031206, | 0.07838703, | 0.00130090, | 0.1582, | −10.9 |
| 3.7, | 0.00000000, | 0.00039379, | 0.07857045, | 0.00103576, | 0.1572, | −11.9 |
| 3.8, | 0.00000000, | 0.00049644, | 0.07867969, | 0.00082388, | 0.1558, | −13.5 |
| 3.9, | 0.00000000, | 0.00062529, | 0.07871994, | 0.00065476, | 0.1544, | −15.6 |
| 4.0, | 0.00000001, | 0.00078693, | 0.07869314, | 0.00051992, | 0.1527, | −18.2 |
| 4.1, | 0.00000001, | 0.00098949, | 0.07859801, | 0.00041249, | 0.1507, | −21.4 |
| 4.2, | 0.00000001, | 0.00124303, | 0.07843000, | 0.00032695, | 0.1484, | −24.2 |
| 4.3, | 0.00000002, | 0.00155992, | 0.07818118, | 0.00025888, | 0.1457, | −29.5 |
| 4.4, | 0.00000003, | 0.00195525, | 0.07783998, | 0.00020474, | 0.1425, | −34.3 |
| 4.5, | 0.00000005, | 0.00244732, | 0.07739094, | 0.00016169, | 0.1388, | −39.4 |
| 4.6, | 0.00000008, | 0.00305804, | 0.07681440, | 0.00012748, | 0.1346, | −44.6 |
| 4.7, | 0.00000013, | 0.00381334, | 0.07608623, | 0.00010030, | 0.1299, | −49.8 |
| 4.8, | 0.00000020, | 0.00474339, | 0.07517769, | 0.00007872, | 0.1247, | −54.6 |
| 4.9, | 0.00000032, | 0.00588245, | 0.07405564, | 0.00006160, | 0.1190, | −58.9 |
| 5.0, | 0.00000049, | 0.00726832, | 0.07268317, | 0.00004802, | 0.1129, | −62.5 |
| 5.1, | 0.00000076, | 0.00894101, | 0.07102096, | 0.00003727, | 0.1065, | −65.4 |
| 5.2, | 0.00000117, | 0.01094045, | 0.06902960, | 0.00002878, | 0.0999, | −67.5 |
| 5.3, | 0.00000179, | 0.01330303, | 0.06667310, | 0.00002208, | 0.0930, | −69.1 |
| 5.4, | 0.00000273, | 0.01605688, | 0.06392358, | 0.00001681, | 0.0860, | −70.3 |
| 5.5, | 0.00000411, | 0.01921621, | 0.06076699, | 0.00001270, | 0.0790, | −71.2 |
| 5.6, | 0.00000613, | 0.02277533, | 0.05720904, | 0.00000949, | 0.0718, | −71.8 |
| 5.7, | 0.00000905, | 0.02670348, | 0.05328045, | 0.00000702, | 0.0646, | −72.3 |
| 5.8, | 0.00001320, | 0.03094196, | 0.04903970, | 0.00000514, | 0.0574, | −72.4 |
| 5.9, | 0.00001901, | 0.03540501, | 0.04457227, | 0.00000371, | 0.0501, | −72.2 |
| 6.0, | 0.00002703, | 0.03998516, | 0.03998516, | 0.00000264, | 0.0430, | −71.5 |
| 6.1, | 0.00003793, | 0.04456276, | 0.03539746, | 0.00000186, | 0.0359, | −70.4 |
| 6.2, | 0.00005252, | 0.04901795, | 0.03092824, | 0.00000129, | 0.0289, | −68.9 |
| 6.3, | 0.00007182, | 0.05324272, | 0.02668457, | 0.00000088, | 0.0221, | −67.2 |
| 6.4, | 0.00009706, | 0.05715037, | 0.02275197, | 0.00000060, | 0.0154, | −65.6 |
| 6.5, | 0.00012973, | 0.06068088, | 0.01918898, | 0.00000040, | 0.0090, | −64.1 |
| 6.6, | 0.00017172, | 0.06380174, | 0.01602627, | 0.00000027, | 0.0026, | −63.0 |
| 6.7, | 0.00022635, | 0.06650499, | 0.01326949, | 0.00000017, | −0.0037, | −62.3 |
| 6.8, | 0.00029350, | 0.06880201, | 0.01090438, | 0.00000011, | −0.0099, | −61.9 |
| 6.9, | 0.00037977, | 0.07071736, | 0.00890279, | 0.00000007, | −0.0161, | −61.7 |
| 7.0, | 0.00048869, | 0.07228296, | 0.00722830, | 0.00000005, | −0.0222, | −61.4 |
| 7.1, | 0.00062587, | 0.07353315, | 0.00584095, | 0.00000003, | −0.0283, | −60. |
| 7.2, | 0.00079828, | 0.07450099, | 0.00470069, | 0.00000002, | −0.0343, | −59. |
| 7.3, | 0.00101463, | 0.07521564, | 0.00376971, | 0.00000001, | −0.0402, | −57. |
| 7.4, | 0.00128558, | 0.07570071, | 0.00301370, | 0.00000001, | −0.0458, | −54. |
| 7.5, | 0.00152428, | 0.07597323, | 0.00240248, | 0.00000001, | −0.0511, | −51. |
| 7.6, | 0.00204673, | 0.07604315, | 0.00191012, | 0.00000000, | −0.0561, | −48. |
| 7.7, | 0.00257227, | 0.07591306, | 0.00151466, | 0.00000000, | −0.0608, | −44. |
| 7.8, | 0.00322401, | 0.07557816, | 0.00229783, | 0.00000000, | −0.0650, | −41. |
| 7.9, | 0.00402915, | 0.07502632, | 0.00094453, | 0.00000000, | −0.0690, | −38. |
| 8.0, | 0.00501914, | 0.07423848, | 0.00074238, | 0.00000000, | −0.0727, | −35. |
| 8.1, | 0.00622941, | 0.07318922, | 0.00058136, | 0.00000000, | −0.0762, | −34. |
| 8.2, | 0.00769865, | 0.07184802, | 0.00045333, | 0.00000000, | −0.0796, | −33. |
| 8.3, | 0.00946717, | 0.07018109, | 0.00035174, | 0.00000000, | −0.0829, | −33. |
| 8.4, | 0.01157428, | 0.06815440, | 0.00027133, | 0.00000000, | −0.0864, | −34. |
| 8.5, | 0.01405446, | 0.06573766, | 0.00020788, | 0.00000000, | −0.0899, | −36. |
| 8.6, | 0.01693235, | 0.06290963, | 0.00015802, | 0.00000000, | −0.0937, | −39. |
| 8.7, | 0.02021684, | 0.05966412, | 0.00011905, | 0.00000000, | −0.0978, | −41. |
| 8.8, | 0.02389526, | 0.05601596, | 0.00008878, | 0.00000000, | −0.1021, | −44. |
| 8.9, | 0.02792875, | 0.05200577, | 0.00006547, | 0.00000000, | −0.1066, | −46. |
| 9.0, | 0.03225042, | 0.04770187, | 0.00004770, | 0.00000000, | −0.1114, | −48. |
| 9.1, | 0.03676756, | 0.04319812, | 0.00003431, | 0.00000000, | −0.1164, | −49. |
| 9.2, | 0.04136840, | 0.03860724, | 0.00002436, | 0.00000000, | −0.1214, | −50. |
| 9.3, | 0.04593262, | 0.03405032, | 0.00001707, | 0.00000000, | −0.1263, | −49. |
| 9.4, | 0.05034366, | 0.02964454, | 0.00001180, | 0.00000000, | −0.1312, | −47. |
| 9.5, | 0.05450025, | 0.02549168, | 0.00000806, | 0.00000000, | −0.1350, | −45. |
| 9.6, | 0.05832483, | 0.02166973, | 0.00000544, | 0.00000000, | −0.1402, | −42. |
| 9.7, | 0.06176749, | 0.01822888, | 0.00000364, | 0.00000000, | −0.1443, | −39. |
| 9.8, | 0.06480566, | 0.01519193, | 0.00000241, | 0.00000000, | −0.1481, | −36. |
| 9.9, | 0.06744042, | 0.01255799, | 0.00000158, | 0.00000000, | −0.1517, | −34. |
| 10.0, | 0.06969093, | 0.01030804, | 0.00000103, | 0.00000000, | −0.1551, | −33.8 |
| 10.1, | 0.07158843, | 0.00841091, | 0.00000067, | 0.00000000, | −0.1585, | −33. |
| 10.2, | 0.07317087, | 0.00682870, | 0.00000043, | 0.00000000, | −0.1619, | −34. |
| 10.3, | 0.07447855, | 0.00552117, | 0.00000028, | 0.00000000, | −0.1655, | −37.5 |
| 10.4, | 0.07555105, | 0.00444878, | 0.00000018, | 0.00000000, | −0.1695, | −41.9 |
| 10.5, | 0.07642521, | 0.00357468, | 0.00000011, | 0.00000000, | −0.1740, | −48.4 |

What is claimed is:

What Is Claimed Is:

1. A fluorocarbon emulsion suitable for use in the tissues, organs and cavities of the body, comprising:
    an aqueous phase;
    a effective amount of a fluorocarbon;
    an emulsifying agent; and
    at least one anti-inflammatory agent which is imidazole, a drug having a chemical structure which includes an imidazolyl group, or combinations thereof.

2. The emulsion of claim 1, further comprising an oligopeptide, an amino acid, or a substituted amino acid.

3. A fluorocarbon suitable for use in the tissues, organs and cavities of the body, comprising:
    an aqueous phase;
    an effective amount of a fluorocarbon;
    an emulsifying agent; and
    at least one anti-inflammatory agent selected from the group consisting of N(7-carboxyheptyl)imidazole, 4-(2-(1-H-imidazol-1-yl)ethoxy)benzoic acid (dazoxiben), or imidazo(1,5-α-pyridine-5-hexanoic acid (CGS 13080).

4. The emulsion of claim 1, wherein the emulsion is capable of carrying oxygen to the tissues.

5. A fluorocarbon emulsion suitable for use in the tissues, organs and cavities of an animal body, comprising
    A continuous aqueous phase;
    an effective amount of fluorocarbon;
    an effective amount of an emulsifying agent; and
    a buffering agent selected from the group consisting of histidine, imidazole, substituted histidine or imidazole compounds retaining the amphoteric site of the imidazole ring, oligopeptides containing histidine, and mixtures thereof.

6. The emulsion of claim 5, wherein said buffering agent comprises a mixture of histidine and imidazole.

7. The emulsion of claim 6, wherein the concentration of imidazole is between about 0.01 and 0.2 molar, and wherein the concentration of histidine is between about 0.01 and 0.2 molar.

8. The emulsion of claim 5, wherein the pH of the emulsion is maintained between 5.3 and 8.9.

9. The emulsion of claim 8, wherein the pH of the emulsion is maintained between about 7.3 and 7.9.

10. The emulsion of claim 8, wherein said buffer maintains said pH at a physiological temperature of about 37° C.

11. The emulsion of claim 8 or 9, wherein said buffer maintains said pH at a temperature below about 30° C.

12. The emulsion of claim 5, wherein the concentration of said buffer is sufficient to provide buffering capacity of at least 20 mmol/L/pH unit between pH values of from about 5.3 to 8.9.

13. The emulsion of claim 1 or 5, wherein said fluorocarbon is a brominated perfluorocarbon.

14. The emulsion of claim 1 or 5, wherein said fluorocarbon is a perfluorocarbon hydride.

15. The emulsion of claim 1 or 5 wherein said fluorocarbon is present in an amount of from about 40% to 125% weight/volume.

16. The emulsion of claim 15, wherein said fluorocarbon is present in an amount greater than about 75% weight/volume.

17. The emulsion of claim 1 or 5 wherein said emulsifying agent is a phospholipid.

18. An emulsion, according to claim 1 or 5 wherein said emulsifying agent is a nonionic surfactant.

19. The emulsion of claim 1 or 5 wherein said emulsifying agent comprises a fluorinated surfactant.

20. An emulsion, according to claim 1 or 5 further comprising an antioxidant agent.

21. An emulsion, according to claim 20, wherein the antioxidant is a tocopherol.

* * * * *

UNITED STATES PATENT AND TRADEMARK OFFICE
CERTIFICATE OF CORRECTION

PATENT NO. : 5,284,645

DATED : February 8, 1994

INVENTOR(S) : Dr. David Long Jr.

It is certified that error appears in the above-identified patent and that said Letters Patent is hereby corrected as shown below:

In column 33, line 29, after "amount of", change "fluorocarbon" to "a fluorocarbon".

Signed and Sealed this

Seventeenth Day of January, 1995

*Attest:*

BRUCE LEHMAN

*Attesting Officer*     *Commissioner of Patents and Trademarks*